United States Patent
Wang et al.

(10) Patent No.: US 7,902,359 B2
(45) Date of Patent: Mar. 8, 2011

(54) DECAHYDRONAPHTHALENE COMPOUNDS

(75) Inventors: Tao Wang, Shanghai (CN); Weihan Zhang, Shanghai (CN); Xiaoqiang Yan, Shanghai (CN); Weiguo Su, Shanghai (CN); Jifeng Duan, Shanghai (CN); Yu Cai, Shanghai (CN)

(73) Assignee: Hutchison MediPharma Enterprises Limited (BS)

( * ) Notice: Subject to any disclaimer, the term of this patent is extended or adjusted under 35 U.S.C. 154(b) by 542 days.

(21) Appl. No.: 11/954,010

(22) Filed: Dec. 11, 2007

(65) Prior Publication Data

US 2008/0139622 A1 Jun. 12, 2008

Related U.S. Application Data

(60) Provisional application No. 60/874,312, filed on Dec. 11, 2006.

(51) Int. Cl.
*C07D 311/78* (2006.01)
*C07D 321/00* (2006.01)
*C07D 239/70* (2006.01)

(52) U.S. Cl. ...... 544/246; 544/249; 549/228; 549/223.2; 549/224

(58) Field of Classification Search ............ 549/228, 549/223, 224; 544/246, 249
See application file for complete search history.

(56) References Cited

FOREIGN PATENT DOCUMENTS

WO 01/85709 A2 11/2001

*Primary Examiner* — Janet L. Andres
*Assistant Examiner* — Raymond Covington
(74) *Attorney, Agent, or Firm* — Finnegan, Henderson, Farrabow, Garrett & Dunner LLP

(57) ABSTRACT

This invention relates to a compound of the following formula:

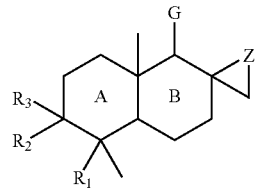

wherein $R_1$, $R_2$, $R_3$, G, and Z are defined herein. It also relates to is methods of treating autoimmune disease, cancer, and atherosclerosis with such a compound.

24 Claims, No Drawings

DECAHYDRONAPHTHALENE COMPOUNDS

CROSS REFERENCE

Pursuant to 35 U.S.C. §119(e), this application claims priority to U.S. Provisional Application 60/874,312, filed on Dec. 11, 2006. The contents of the provisional application are incorporated by reference.

BACKGROUND

Tumor necrosis factor alpha (TNFα), a mononuclear cytokine, possesses various biological activities, such as killing or inhibiting growth of cancer cells and enhancing phagocytosis of neutrophilic granulocyte. Interleukin-1 beta (IL-1β), a cytokine secreted by monocyte macrophages and dendritic cells, mediates immune and inflammatory responses. Nuclear factor-kappa B (NF-κB), a pro-inflammatory transcription factor, upregulates cytokines (e.g., TNFα and IL-1β) and thereby mediates inflammatory responses. Inducible nitric oxide synthase (iNOS) is induced by endotoxins or cytokines (e.g., TNFα and IL-1β). It catalyzes the production of nitric oxide, an important pleiotropic molecule, from L-arginine and oxygen.

TNFα, IL-1β, NF-κB, and iNOS all play critical roles in important physiological and pathological processes. A wide range of diseases, e.g., autoimmune disease, cancer, atherosclerosis, and diabetes, can be treated by modulating their expression or activity. See, e.g., Ogata H, Hibi T. et al *Curr Pharm Des.* 2003; 9(14): 1107-13; Taylor P C. et al *Curr Pharm Des.* 2003; 9(14): 1095-106; Fan C., et al. *J. Mol. Med.* 1999, 77, 577-592; and Alcaraz et al., *Current Pharmaceutical Design,* 2002: 8, 215.

SUMMARY

This invention is based on a surprising discovery that a number of novel compounds inhibit expression of TNFα, IL-1β, and iNOS, and the activity of NF-κB.

One aspect of this invention features compounds of the following formula I:

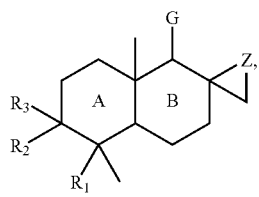

Formula I in which $R_1$ is H, OH, CHO, or $CH_2NR_aR_b$; each of $R_2$ and $R_3$, independently, is H, OH, or $NR_aR_b$, or $R_2$ and $R_3$ together are =O or $=NR_c$; or $R_1$ is $CH_2OH$; each of $R_2$ and $R_3$, independently, is H or $NR_aR_b$, or $R_2$ and $R_3$ together are =O or $=NR_c$; in which each of $R_a$ and $R_b$, independently, is H, alkyl, cycloalkyl, heterocycloalkyl, aryl, or heteroaryl; or $R_a$ and $R_b$, together with the N atom to which they are attached, are heterocycloalkyl or heteroaryl; and $R_c$ is H, alkyl, cycloalkyl, heterocycloalkyl, aryl, heteroaryl, hydroxy, or alkoxy; or $R_1$, $R_2$, and $R_3$, together with ring A which they are attached to, are:

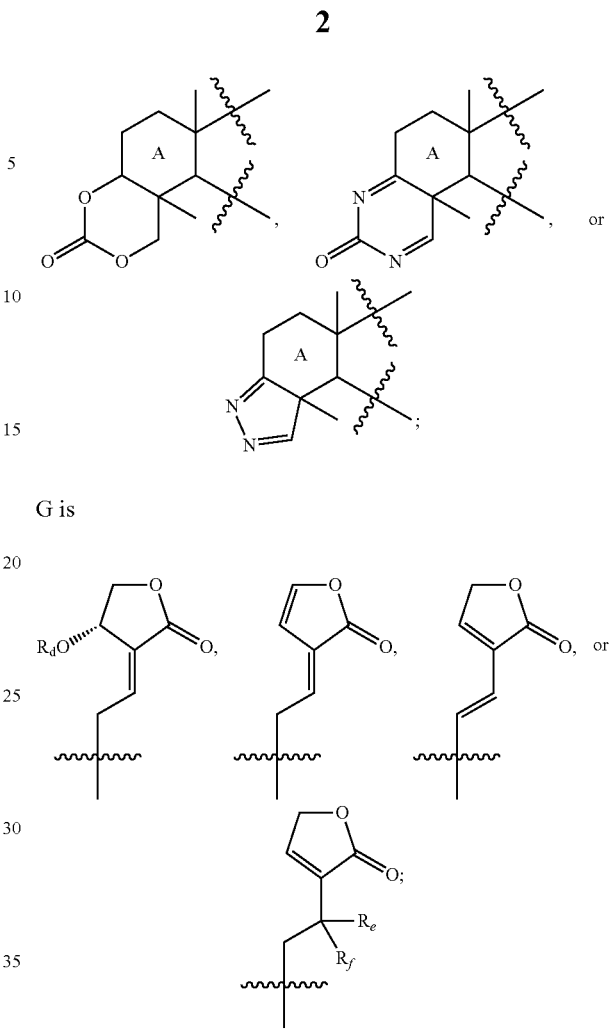

G is

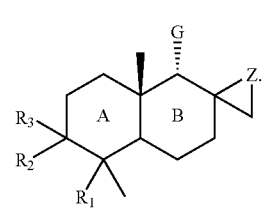

in which $R_d$ is H, alkyl, cycloalkyl, heterocycloalkyl, aryl, heteroaryl, $R_aCO$, or $R_aR_b NHCO$, each of $R_{a'}$ and $R_{b'}$, independently, being H, alkyl, cycloalkyl, heterocycloalkyl, aryl, or heteroaryl; each of $R_e$ and $R_f$, independently, is H, alkoxy, aryloxy, heterocycloalkoxy, heteroaryloxy, alkylthio, arylthio, heterocycloalkylthio, heteroarylthio, or $NR_{c'}R_{d'}$, $R_{c'}$ and $R_{d'}$, independently, being H, alkyl, cycloalkyl, heterocycloalkyl, aryl, or heteroaryl, or $R_{c'}$, $R_{d'}$, and the nitrogen atom to which they are attached, together, being heterocycloalkyl or heteroaryl; and Z is O or a bond.

The compounds described above include their pharmaceutically acceptable salts, hydrate, and prodrugs, if applicable. They can occur as racemic mixtures, single enantiomers, individual diastereomers, diastereomeric mixtures, and cis- or trans-isomeric forms. All such isomeric forms are contemplated. As an example, the compounds of this invention can be isomers having the stereochemistry as shown in formula II below:

Formula II

One subset of the compounds of this invention features that $R_1$ is H, and $R_2$ and $R_3$ together are =O; or each of $R_1$ and $R_2$ is H, and R$_3$ is OH; or R$_1$, R$_2$, and R$_3$, together with ring A which they are attached to, are

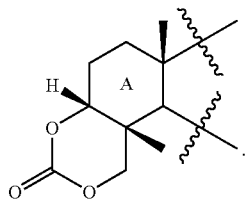

Another subset features that G is

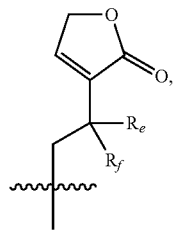

in which R$_e$ can be H and R$_f$ can be heteroaryl or NR$_c$,R$_{d'}$, R$_{c'}$ being H and R$_{d'}$ being alkyl. Still another subset features that Z is a bond.

The term "alkyl," unless stated otherwise, refers to a straight or branched hydrocarbon containing 1-20 carbon atoms. Alkyl may contain one or more carbon-carbon double or triple bonds. Examples of alkyl groups include, but are not limited to, methyl, ethyl, n-propyl, i-propyl, n-butyl, i-butyl, and t-butyl.

The term "cycloalkyl," unless stated otherwise, refers to a saturated and partially unsaturated cyclic hydrocarbon group having 3 to 12 carbon atoms. Examples of cyclyl groups include, but are not limited to, cyclopropyl, cyclobutyl, cyclopentyl, cyclopentenyl, cyclohexyl, cyclohexenyl, cycloheptyl, and cyclooctyl.

The term "heterocycloalkyl" refers to a saturated or partially unsaturated cyclic hydrocarbon group having 2 to 12 carbon atoms and at least one heteroatom selected from N, O, and S.

The term "aryl," unless stated otherwise, refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl.

The terms "alkoxy," "cycloalkyloxy," "aryloxy," "heteroaryloxy," and "heterocyclalkyloxy," refer to radicals alkyl-O, cycloalkyl-O, aryl-O, heteroaryl-O, and heterocycloalkyl-O, respectively. Similarly, "alkylthio," "cycloalkylthio," "arylthio," "heteroarylthio," and "heterocyclalkylthio," refer to radicals alkyl-S, cycloalkyl-S, aryl-S, heteroaryl-S, and heterocycloalkyl-S, respectively.

Alkyl, cycloalkyl, heterocycloalkyl, aryl, heteroaryl can be either substituted or unsubstituted. For examples, these moieties can be substituted with groups containing zero to six heteroatoms selected from halogen, oxygen, sulfur, and nitrogen. Possible substituents on alkenyl, alkynyl, cycloalkyl, heterocycloalkyl, aryl, and heteroaryl include alkyl, alkenyl, alkynyl, cycloalkyl, heterocycloalkyl, alkoxy, aryl, aryloxy, heteroaryl, heteroaryloxy, amino, alkylamino, dialkylamino, arylamino, diarylamino, hydroxy, halogen, thio, alkylthio, arylthio, alkylsulfonyl, arylsulfonyl, acylamino, aminoacyl, amidino, guanidino, ureido, cyano, nitro, acyl, acyloxy, carboxyl, and carboxylic ester. Possible substituents on alkyl include all of the above-said substituents except alkyl.

Shown below are exemplary compounds of this invention:

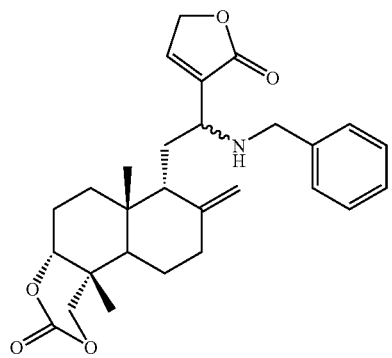

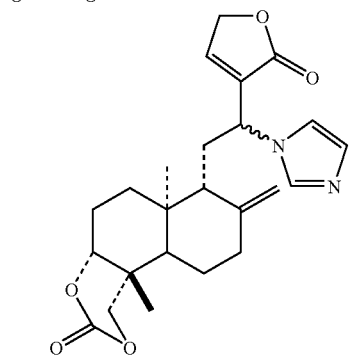

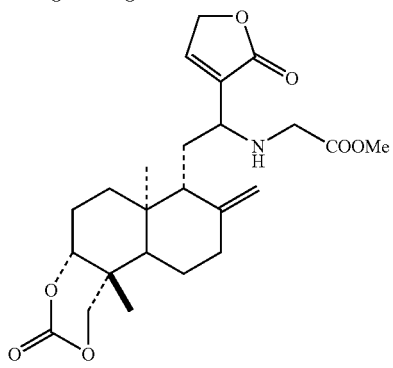

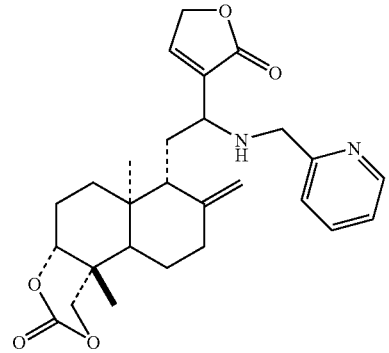

5
-continued
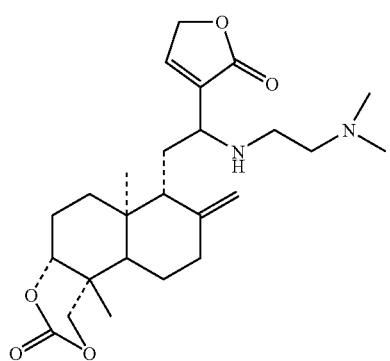
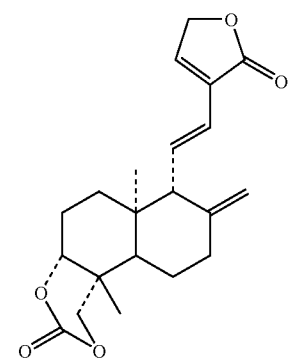
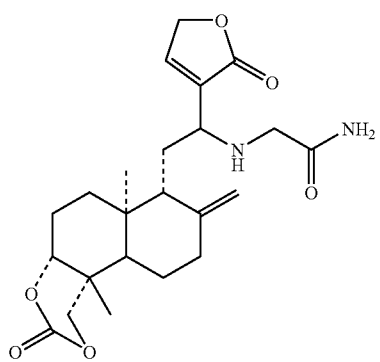
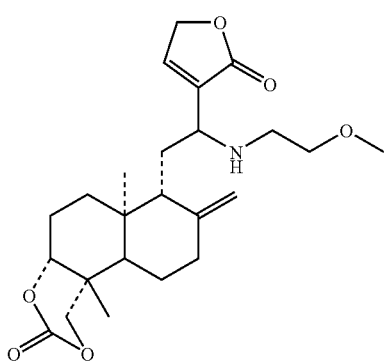
6
-continued
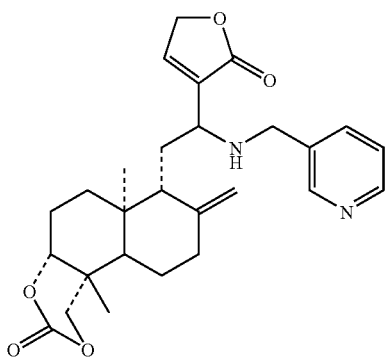
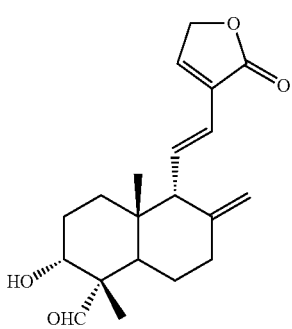
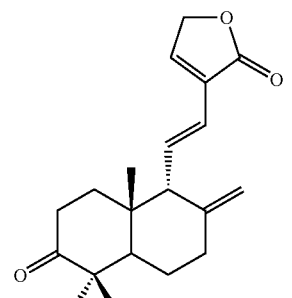
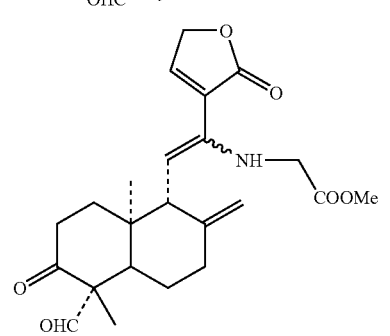
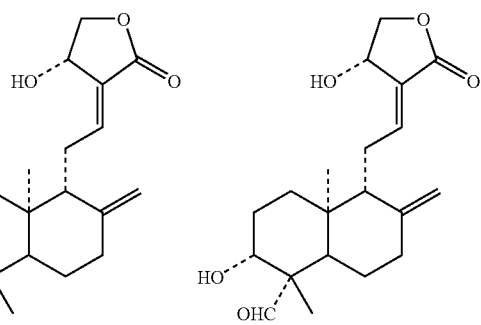

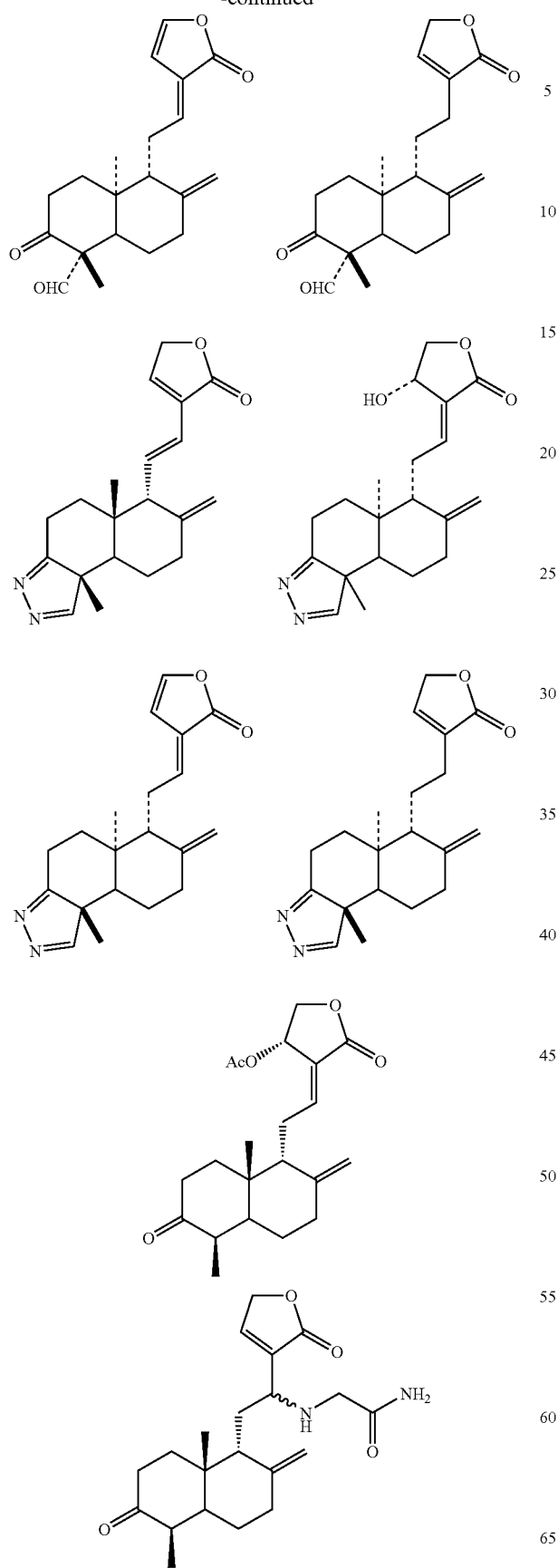
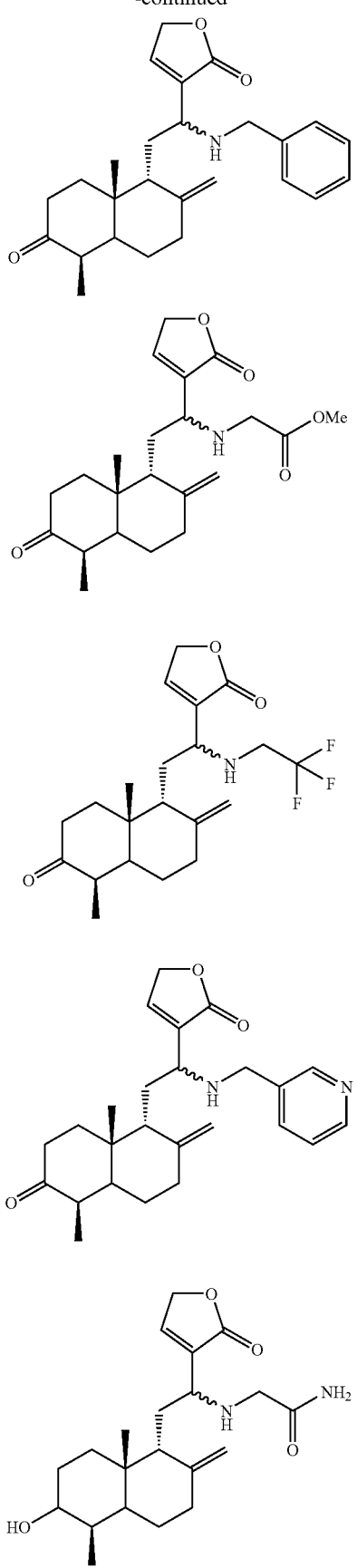

-continued

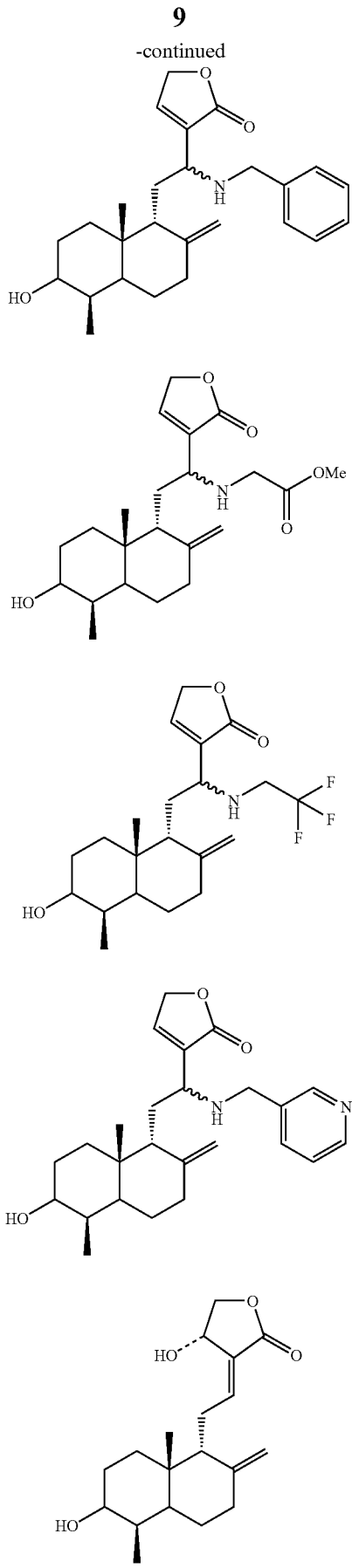

-continued

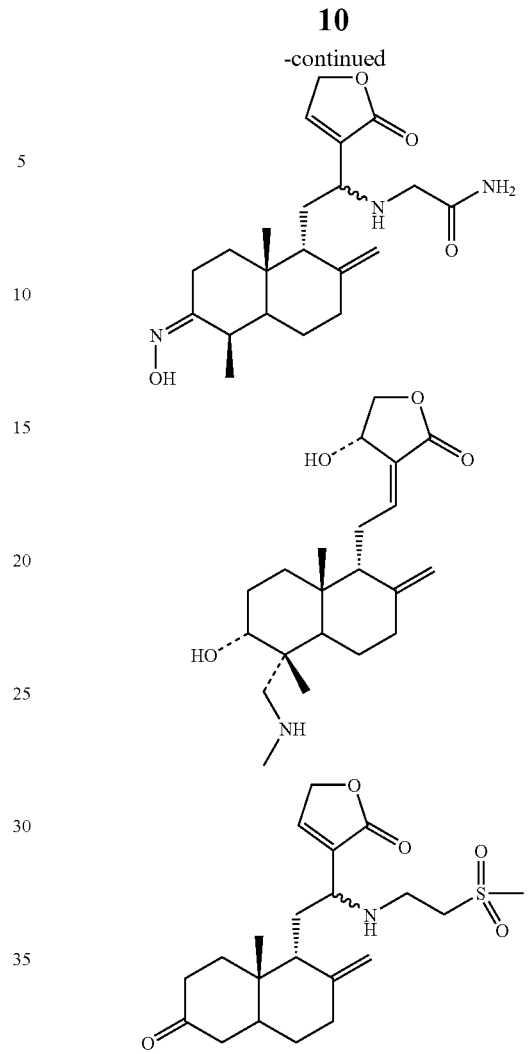

Another aspect of this invention features a method of inhibiting the expression of TNFα, IL-1β, or iNOS, or inhibiting the activity of NF-κB, by contacting a cell in need thereof with an effective amount of one or more of the above described compounds.

Still another aspect of this invention features a method of treating disease associated with TNFα, IL-1β, iNOS, or NF-κB (e.g., autoimmune disease, cancer, atherosclerosis, or diabetes) by administering to a subject in need thereof an effective amount of one or more the just-described compounds.

Also within the scope of this invention is a composition containing one or more of the above-described compounds and a pharmaceutically acceptable carrier for use in treating autoimmune disease, cancer, atherosclerosis, or diabetes, as well as the use of such a composition for the manufacture of a medicament for treating such a disease.

The details of one or more embodiments of the invention are set forth in the description below. Other features, objects, and advantages of the invention will be apparent from the description and from the claims.

DETAILED DESCRIPTION

The compounds of this invention can be synthesized from commercially available starting materials via conventional chemical transformations. For examples, some of the compounds can be made by modifying andrographolide, which is a naturally occurring lactone compound isolated from plants such as *Andrographis paniculata* Nees. See U.S. patent application Ser. No. 11/078,198.

Scheme 1 below illustrates a synthetic route to a compound of this invention by modifying andrographolide.

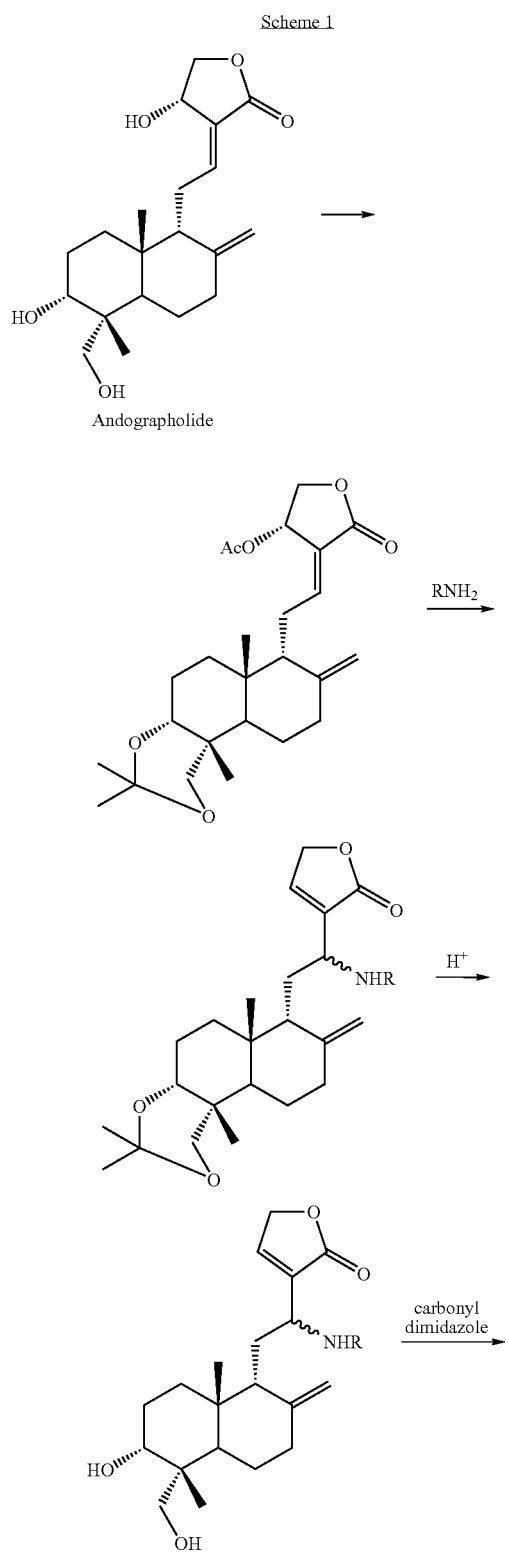

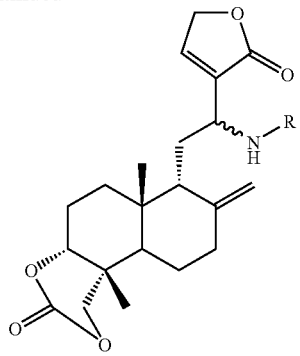

As shown in the above scheme, andrographolide is first protected by the method described in Nanduri, et al., *Tetrahedron Letters*, 2004, 45, 4883-4886. The protected andrographolide compound is reacted with amine and then deprotected to afford 12-amino-14-deoxyandrographolide. This compound is reacted with carbonyl diimidazole to form a 12-amino-3,19-O-carbonate-14-deoxyandrographolide compound.

Scheme 2 below shows another synthetic route from andrographolide to a compound of this invention. Briefly, one can oxidize the protected andraholide compound to afford 3,19-dioxo-14-deoxyandrographolide, and then decarbonylate the resulting compound to afford 19-dehydroxymethyl-14-deoxyandrographolide, which is subsequently converted into an 12-amino-19-dehydroxymethyl-14-3-oxo-deoxyandrographolide compound by reacting it with amine. The resulting amino compound is reduced with NaBH$_4$ to give an 12-amino-19-dehydroxymethyl-14-3-hydroxy-deoxyandrographolide compound.

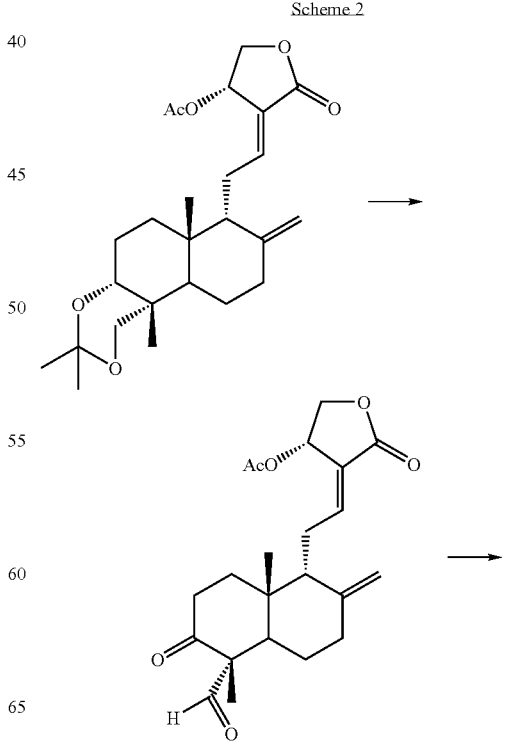

-continued

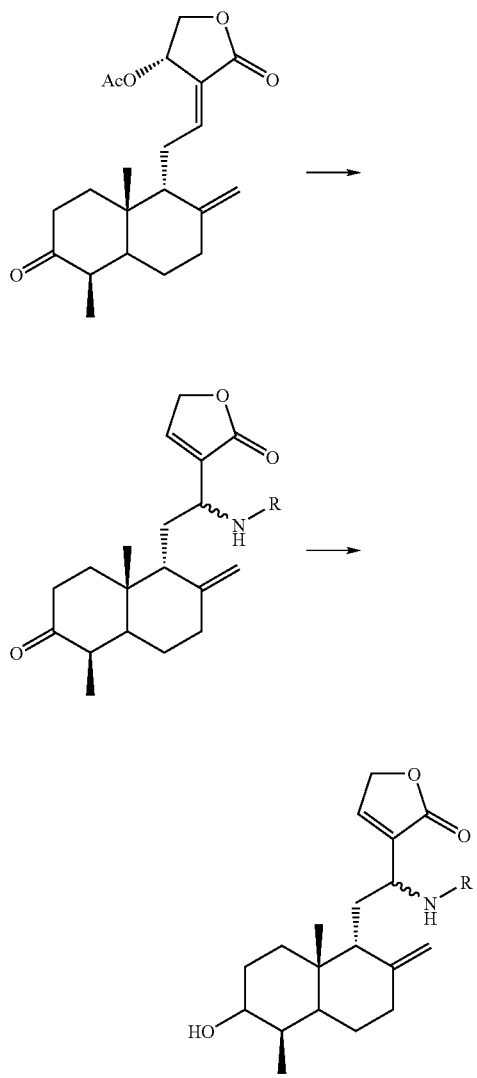

The compounds thus obtained can be further purified by column chromatography, high performance liquid chromatography, or crystallization.

Other compounds of this invention can be synthesized in a manner similar to that illustrated in the above two schemes.

Synthetic chemistry transformations and protecting group methodologies (protection and deprotection) required in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of this invention exhibit inhibitory effect against expression of TNFα, IL-1β, and iNOS and activity of NF-κB or reduce cell responses to these biological agents. Thus, this invention relates to a method of inhibiting expression of TNFα, IL-1β, and iNOS and activity of NF-κB by contacting cells with an effective amount of one or more of the compounds of this invention. Also included in this invention is a method of treating autoimmune disease, cancer, atherosclerosis caused by over production of cytokines or activation of NF-κB by administering to a subject who needs the treatment an effective amount of one or more of the compounds. Examples of the autoimmune disease includes, but are not limited to, inflammatory bowel disease (including Crohn's disease and ulcerative colitis), multiple sclerosis, arthritis, psoriasis, systemic lupus erythematosus, polymyositis/dermatomyositis, acute myelogenous leukemia, Parkinson's disease, AIDS dementia complex, and Alzheimer's disease. The term "treating" refers to administering one or more of the compounds of this invention to a subject, who has autoimmune disease, cancer, or atherosclerosis, a symptom of the disease, or a predisposition toward the disease, with the purpose to prevent, cure, heal, alleviate, relieve, alter, remedy, ameliorate, improve, or affect the disease, the symptom, or the predisposition. "An effective amount" refers to the amount of a compound which is required to confer the desired effect on the subject. Effective amounts vary, as recognized by those skilled in the art, depending on route of administration, excipient usage, and the possibility of co-usage with other therapeutic treatments such as use of other active agents.

To practice the above-described methods, a composition having one or more of the compounds of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active andrographolide derivative can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The compounds of this invention can be preliminarily screened by an in vitro assay for one or more of their desired activities, e.g., inhibiting expression of TNFα, IL-1β, or iNOS, or activity of NF-κB. Compounds that demonstrate high activities in the preliminary screening can further be screened for their efficacy by in vivo assays. For example, a test compound can administered to an animal model (e.g., a mouse having autoimmune disease, cancer, or atherosclerosis) and its therapeutic effect is then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All of the publications cited herein, including patents or patent applications, are hereby incorporated by reference in their entirety.

Example 1

Synthesis of
12-N-benzylamino-14-deoxyandrographolide
(Compound 1)

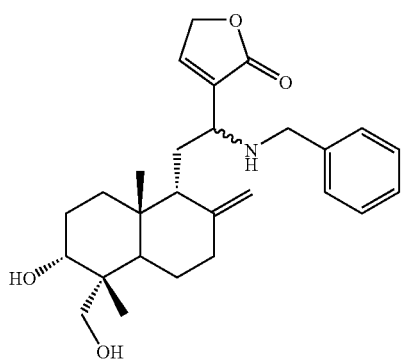

Compound 1

A solution of benzylamine (3 mL, 30 mmol) in 10 mL ethyl ether was added to a solution of 3,19-O-isopropylidene-14-acetylandrographolide (Nanduri, et al., *Tetrahedron Letters*, 2004, 45, 4883-4886) (3.9 g, 9 mmol) in diethyl ether (100 mL). The mixture was stirred at room temperature for 3 hours. Then, 1N HCl (100 mL) was added. After being stirred for another 1 hour, the mixture was neutralized by saturated $NaHCO_3$ aqueous solution to adjust pH to 7.5. The organic layer was removed and the aqueous layer was extracted with dichloromethane (3×50 mL). The organic layers were combined, dried over $Na_2SO_4$, concentrated, and purified by chromatography to afford 12-N-benzylamino-14-deoxyandrographolide (yield: 72%).

MS (m/z): 440.3 (M+1)

$^1$H NMR ($CDCl_3$, 300 MHz): 7.30 (m, 5H), 7.16 (m, 1H), 4.81 (s, 1H), 4.79 (m, 2H), 4.58 (s, 1H), 4.19 (d, J=11.3 Hz), 3.72 (m, 2H), 3.32 (d, J=11.0 Hz, 1H), 1.25 (s, 3H), 0.60 (s, 3H).

Example 2

1 Synthesis of
12-N-glycinamide-14-deoxyandrographolide
(Compound 2)

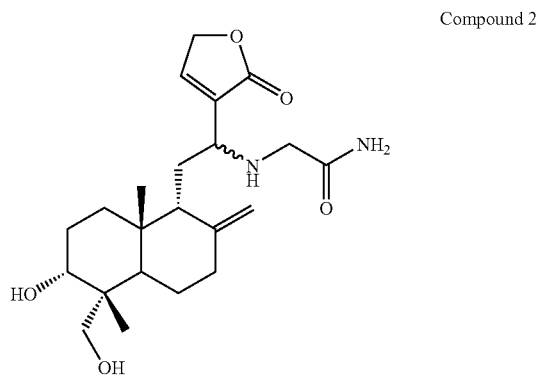

Compound 2

A mixture of glucinamide hydrochloride (0.45 g, 3 mmol) and $K_2CO_3$ (0.41 g, 3 mmol) in 20 mL ethanol was stirred for 15 min. Then, a solution of 3,19-O-isopropylidiene-14-acetylandrographolide (0.43 g, 1 mmol) in 50 mL diethyl ether was added. After 5 hours, the mixture was treated with 1N HCl (10 mL), stirred for 1 additional hour, and then neutralized with a saturated $NaHCO_3$ aqueous solution to adjust the pH to 7.5. The ether layer was removed and the aqueous layer was extracted with dichloromethane (3×30 mL). The organic layers were combined, dried over $Na_2SO_4$, concentrated, and purified by chromatography to afford 12-N-glycinamide-14-deoxyandrographolide (yield: 65%).

MS (m/z): 407.2 (M+1)

$^1$H NMR ($CDCl_3$, 300 MHz): 7.23 (m, 1H), 4.83 (s, 1H), 4.80 (m, 2H), 4.62 (s, 1H), 4.16 (d, J=11.3 Hz, 1H), 3.40 (m, 2H), 3.32 (d, J=11.0 Hz, 1H), 1.20 (s, 3H), 0.60 (s, 3H).

Examples 3-19

Compounds 3-19 were each synthesized in a manner similar to that described in Example 2.

| No. | Name | Structure | ¹H NMR(CDCl₃) |
|---|---|---|---|
| 3 | 12-N-[1-(thiophen-3-ylmethylamino)]-14-deoxyandrographolide | 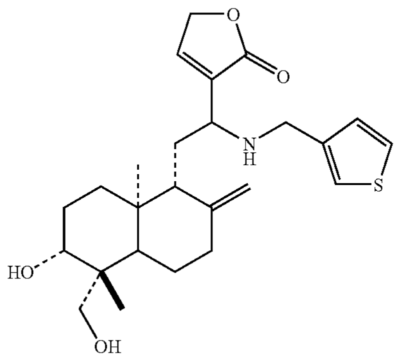 | 7.23 (m, 2H), 6.75 (m, 2H), 4.83 (s, 1H), 4.80 (m, 2H), 4.62 (s, 1H), 3.45 (m, 2H), 1.20 (s, 3H), 0.60 (s, 3H) |
| 4 | 12-N-[1-(4-methylthiazol-2-ylamino)]-14-deoxyandrographolide | 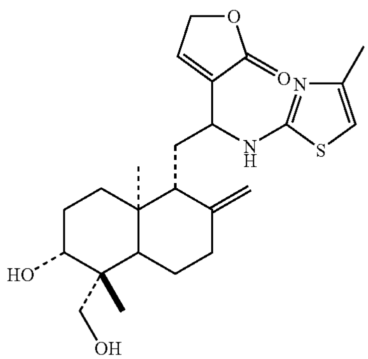 | 7.25 (m, 1H), 6.05 (m, 1H), 4.90 (m, 2H), 4.83 (s, 1H), 4.62 (s, 1H), 2.50 (s, 3H), 1.20 (s, 3H), 0.60 (s, 3H) |
| 5 | 12-N-[O-methylglycino]-14-deoxyandrographolide | 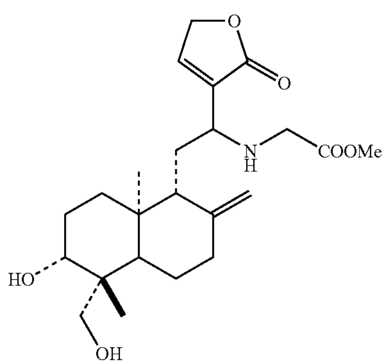 | 7.25 (m, 1H), 4.90 (m, 2H), 4.83 (s, 1H), 4.62 (s, 1H), 3.80 (s, 3H), 1.20 (s, 3H), 0.60 (s, 3H). |
| 6 | 12-N-[1-(allylamino]-14-deoxyandrographolide | 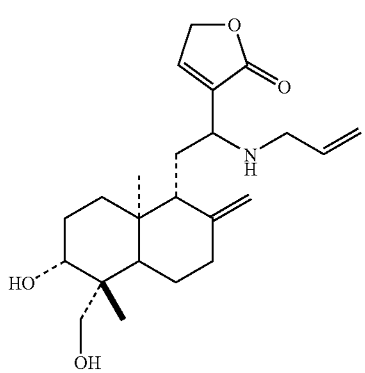 | 7.26 (m, 1H), 5.80 (m, 1H), 5.20 (m, 2H), 4.90 (m, 2H), 4.83 (s, 1H), 4.62 (s, 1H), 1.20 (s, 3H), 0.60 (s, 3H) |

-continued

| No. | Name | Structure | ¹H NMR(CDCl₃) |
|---|---|---|---|
| 7 | 12-N-[1-pyridin-2-ylmethylamino]-14-deoxyandrographolide | 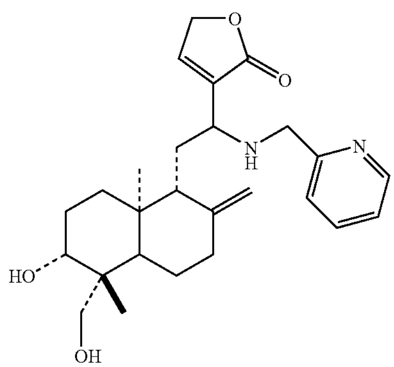 | 8.50 (m, 1H), 7.82 (m, 1H), 7.53 (m, 2H), 7.26 (m, 1H), 4.90 (m, 2H), 4.83 (s, 1H), 4.62 (s, 1H), 1.20 (s, 3H), 0.60 (s, 3H) |
| 8 | 12-N-[1-(cyclopropylamino)]-14-deoxyandrographolide | 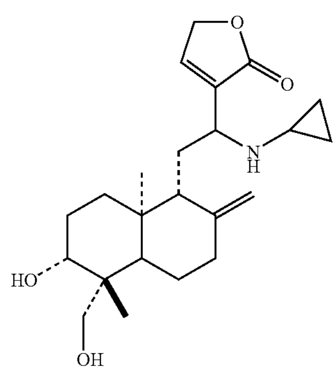 | 7.27 (m, 1H), 4.90 (m, 2H), 4.83 (s, 1H), 4.62 (s, 1H), 1.20 (s, 3H), 0.60 (s, 3H), 0.43 (m, 2H), 0.18 (m, 2H) |
| 9 | 12-N-[2-pyridin-2-yl)ethylamino]-14-deoxyandrographolide | 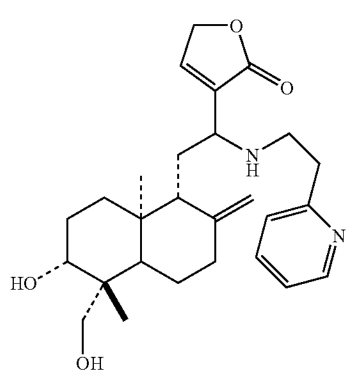 | 8.52 (m, 1H), 7.82 (m, 1H), 7.53 (m, 2H), 7.26 (m, 1H), 4.90 (m, 2H), 4.83 (s, 1H), 4.65 (s, 1H), 2.8 (m, 2H), 3.0 (m, 2H), 1.20 (s, 3H), 0.60 (s, 3H) |
| 10 | 12-N-[2-hydroxy-ethylamino]-14-deoxyandrographolide | 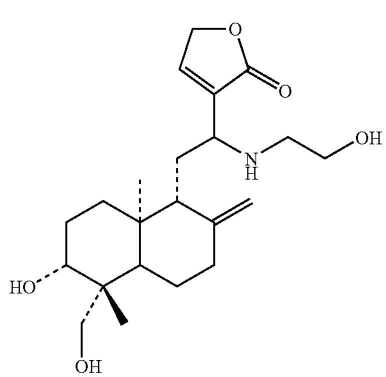 | 7.27 (m, 1H), 4.90 (m, 2H), 4.83 (s, 1H), 4.62 (s, 1H), 3.6 (m, 2H), 2.8 (m, 2H), 1.20 (s, 3H), 0.60 (s, 3H) |

-continued
| No. | Name | Structure | $^1$H NMR(CDCl$_3$) |
|---|---|---|---|
| 11 | 12-N-[2-(dimethylamino)ethylamino]-14-deoxyandrographolide | 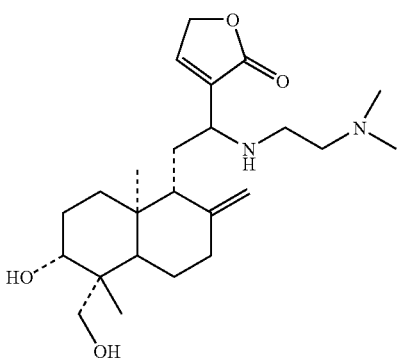 | 7.40 (m, 1H), 4.90 (m, 2H), 4.83 (s, 1H), 4.62 (s, 1H), 2.62 (m, 2H), 2.48 (m, 2H), 2.3 (s, 6H), 1.20 (s, 3H), 0.60 (s, 3H) |
| 12 | 12-N-[2-methoxyethylamino]-14-deoxyandrographolide | 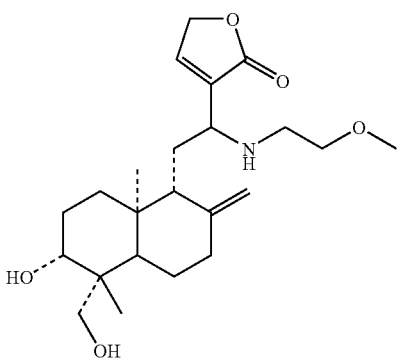 | 7.27 (m, 1H), 4.90 (m, 2H), 4.83 (s, 1H), 4.62 (s, 1H), 3.5 (m, 2H), 3.3 (s, 3H), 2.8 (m, 2H), 1.20 (s, 3H), 0.60 (s, 3H) |
| 13 | 12-N-[1-pyridin-3-ylmethylamino]-14-deoxyandrographolide | 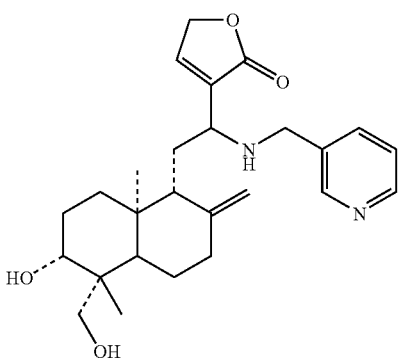 | 8.70 (m, 1H), 8.51 (m, 1H), 7.53 (m, 2H), 7.26 (m, 1H), 4.90 (m, 2H), 4.83 (s, 1H), 4.62 (s, 1H), 1.20 (s, 3H), 0.60 (s, 3H) |
| 14 | 12-N-[1-(4-fluorobenzylamino]-14-deoxyandrographolide | 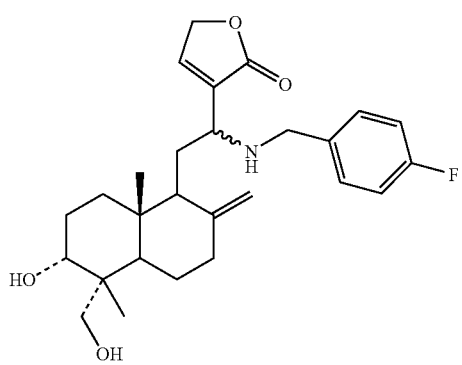 | 7.27 (m, 1H), 7.06 (m, 2H), 6.89 (m, 2H), 4.90 (m, 2H), 4.83 (s, 1H), 4.62 (s, 1H), 1.20 (s, 3H), 0.60 (s, 3H) |

| No. | Name | Structure | ¹H NMR(CDCl₃) |
|-----|------|-----------|----------------|
| 15 | 12-N-[1-(4-chlorobenzylamino]-14-deoxyandrographolide | 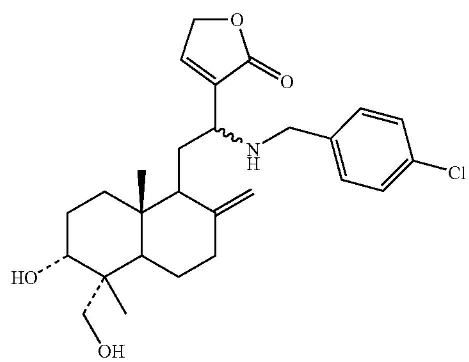 | 7.27 (m, 1H), 7.20 (m, 2H), 7.11 (m, 2H), 4.90 (m, 2H), 4.83 (s, 1H), 4.62 (s, 1H), 1.20 (s, 3H), 0.60 (s, 3H) |
| 16 | 12-N-[1-(3-chlorobenzylamino]-14-deoxyandrographolide | 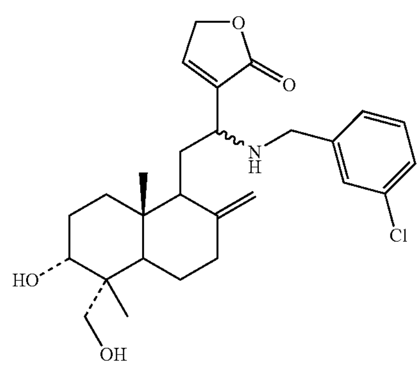 | 7.27 (m, 1H), 7.10 (m, 2H), 7.08 (m, 1H), 6.92 (m, 1H), 4.90 (m, 2H), 4.83 (s, 1H), 4.62 (s, 2H), 1.20 (s, 3H), 0.60 (s, 3H) |
| 17 | 12-N-[1-(2-chlorobenzylamino]-14-deoxyandrographolide | 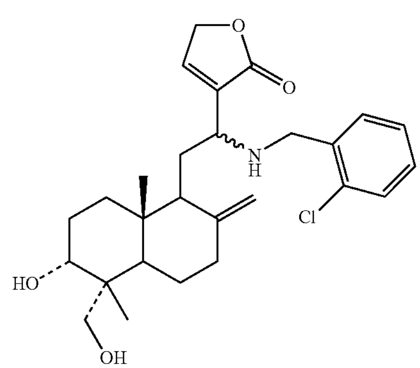 | 7.27 (m, 1H), 7.10 (m, 4H), 4.90 (m, 2H), 4.83 (s, 1H), 4.62 (s, 1H), 1.20 (s, 3H), 0.60 (s, 3H) |
| 18 | 12-N-[1-(4-(methylsulfonyl)benzylamino]-14-deoxyandrographolide | 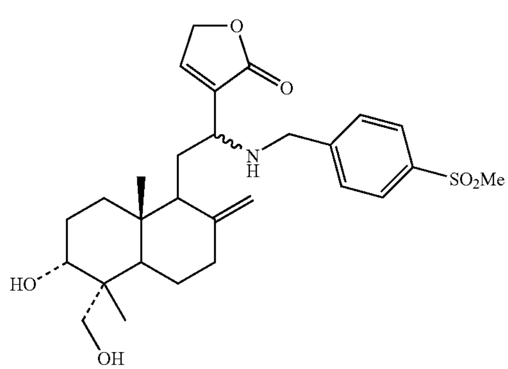 | 7.80 (m, 2H), 7.40 (m, 2H), 7.27 (m, 1H), 4.90 (m, 2H), 4.85 (s, 1H), 4.62 (s, 1H), 2.81 (s, 3H), 1.20 (s, 3H), 0.60 (s, 3H) |

-continued

| No. | Name | Structure | $^1$H NMR(CDCl$_3$) |
|---|---|---|---|
| 19 | 12-N-[2,2,2-trifluoroethylamino]-14-deoxyandrographolide | 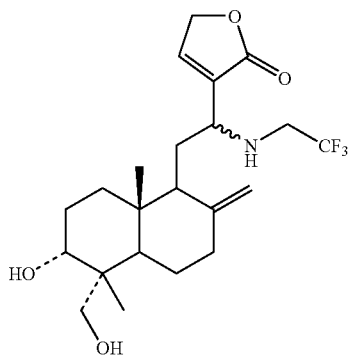 | 7.27 (m, 1H), 4.90 (m, 2H), 4.83 (s, 1H), 4.62 (s, 1H), 3.1 (m, 2H), 1.20 (s, 3H), 0.60 (s, 3H) |

Example 20

Synthesis of 12-N-benzylamino-3,19-O-carbonate-14-deoxyandrographolide (Compound 20)

Compound 20

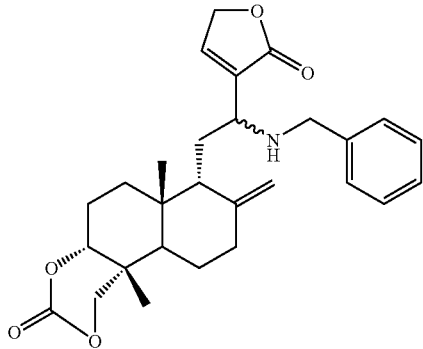

To a solution of 12-N-benzylamino-14-deoxyandrapholide (1 g, 2.5 mmol) in 20 mL dry CH$_3$CN was added carbonyl diimidazole (0.81 g, 5 mmol). The mixture was stirred at room temperature overnight, diluted with water, and then extracted with dichloromethane (3×20 mL). The combined organic layers were dried over Na$_2$SO$_4$, concentrated, and then purified by chromatography to afford the title compound (yield: 56%).

MS (m/z): 466.2 (M+1)

$^1$H NMR (CDCl$_3$, 300 MHz): 7.32 (m, 5H), 7.26 (m, 1H), 4.81 (s, 1H), 4.79 (m, 2H), 4.58 (s, 1H), 3.9 (m, 1H), 3.72 (m, 2H), 1.25 (s, 3H), 0.60 (s, 3H).

Examples 21-28

Compounds 21-28 were each synthesized in a manner similar to that described in Example 20.

| No. | Name | Structure | NMR |
|---|---|---|---|
| 21 | 12-N-[2-(1H-imidazol-1-yl]-3,19-O-carbonate-14-deoxyandrographolide | 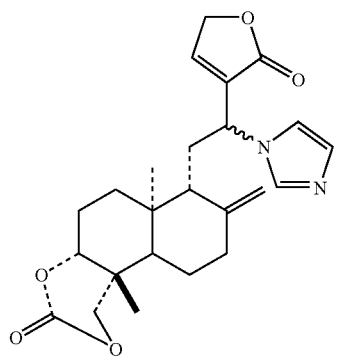 | 7.45 (m, 1H), 7.27 (m, 1H), 6.95 (m, 2H), 4.90 (m, 2H), 4.83 (s, 1H), 4.63 (s, 1H), 3.9 (m, 1H), 1.20 (s, 3H), 0.60 (s, 3H) |

-continued

| No. | Name | Structure | NMR |
|---|---|---|---|
| 22 | 12-N-[O-methylglycino]-3,19-O-carbonate-14-deoxyandrographolide | 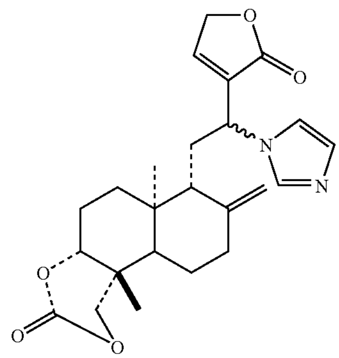 | 7.25 (m, 1H), 4.90 (m, 2H), 4.83 (s, 1H), 4.62 (s, 1H), 3.9 (m, 1H), 3.80 (s, 3H), 1.20 (s, 3H), 0.60 (s, 3H) |
| 23 | 12-N-[1-pyridin-2-ylmethylamino]-3,19-O-[carbonate]-14-deoxyandrographolide | 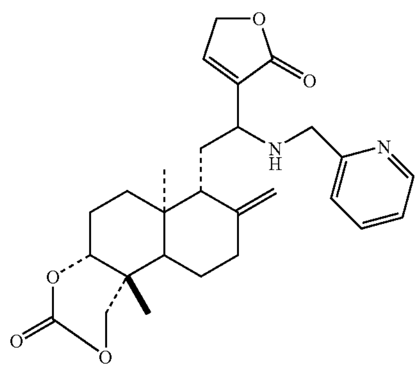 | 8.50 (m, 1H), 7.82 (m, 1H), 7.53 (m, 2H), 7.26 (m, 1H), 4.90 (m, 2H), 4.83 (s, 1H), 4.62 (s, 1H), 3.9 (m, 1H), 1.20 (s, 3H), 0.60 (s, 3H) |
| 24 | 12-N-[2-(dimethylamino)ethylamino]-3,19-O-carbonate-14-deoxyandrographolide | 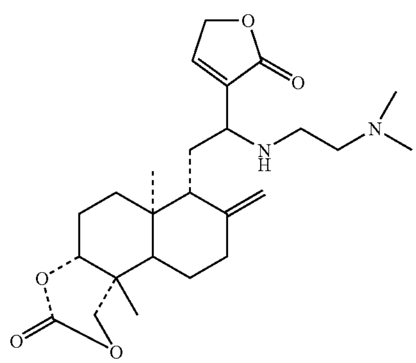 | 7.40 (m, 1H), 4.90 (m, 2H), 4.83 (s, 1H), 4.62 (s, 1H), 3.9 (m, 1H), 2.62 (m, 2H), 2.48 (m, 2H), 2.3 (s, 6H), 1.20 (s, 3H), 0.60 (s, 3H) |
| 25 | 11,12-didehydro-3,19-O-carbonate-14-deoxyandrographolide | 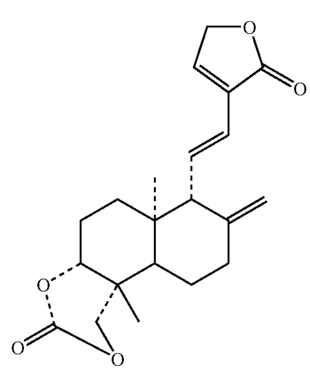 | 7.10 (t, J = 1.5 Hz, 1H), 6.85 (m, 1H), 6.13 (m, 1H), 4.88 (s, 1H), 4.78 (m, 2H), 4.60 (s, 1H), 3.8 (m, 1H), 1.25 (s, 3H), 0.65 (s, 3H) |

| No. | Name | Structure | NMR |
|-----|------|-----------|-----|
| 26 | 12-N-glycinamide-3,19-O-carbonate-14-deoxyandrographolide | 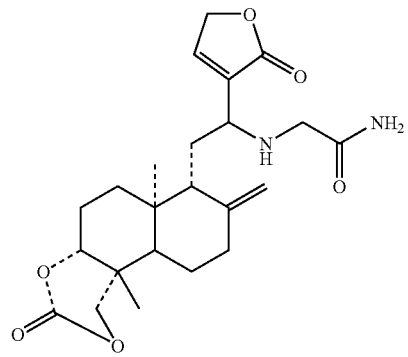 | 7.23 (m, 1H), 4.83 (s, 1H), 4.80 (m, 2H), 4.62 (s, 1H), 3.8 (m, 1H), 3.40 (m, 2H), 1.22 (s, 3H), 0.63 (s, 3H) |
| 27 | 12-N-[2-methoxyethylamino]-3,19-O-carbonate-14-deoxyandrographolide | 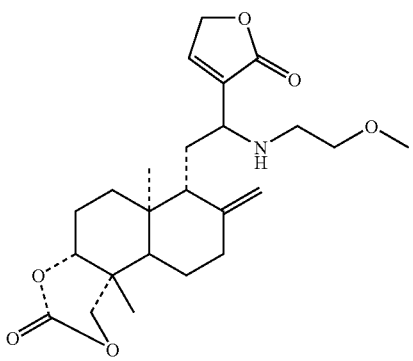 | 7.27 (m, 1H), 4.90 (m, 2H), 4.83 (s, 1H), 4.62 (s, 1H), 3.8 (m, 1H), 3.5 (m, 2H), 3.3 (s, 3H), 2.8 (m, 2H), 1.23 (s, 3H), 0.62 (s, 3H) |
| 28 | 12-N-[1-pyridin-3-ylmethylamino]-3,19-O-carbonate-14-deoxyandrographolide | 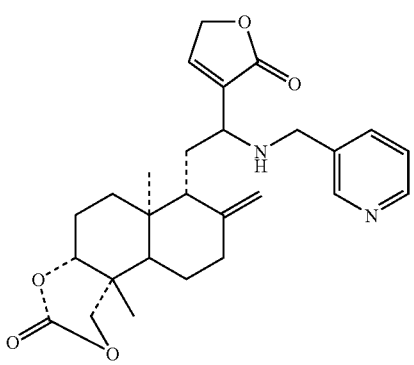 | 8.72 (m, 1H), 8.50 (m, 1H), 7.51 (m, 2H), 7.26 (m, 1H), 4.90 (m, 2H), 4.83 (s, 1H), 4.62 (s, 1H), 3.7 (m, 1H), 1.20 (s, 3H), 0.60 (s, 3H) |

Example 29

Synthesis of 8,17-epoxide-12-N—(O-methylgly-cino)-14-deoxyandrographolide (Compound 29)

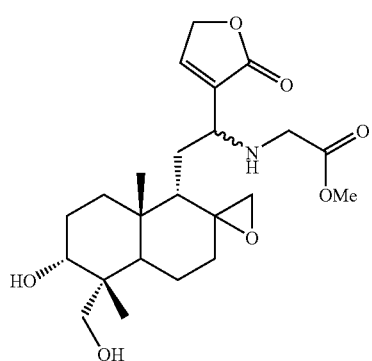

Compound 29

To a solution of 12-N—(O-methylglycino)-14-deoxyandrographolide (0.8 g, 1.9 mmol) in 25 mL $CH_2Cl_2$ was added $K_2CO_3$ (0.138 g, 1 mmol) and m-chloroperoxybenzoic acid (2.3 mmol). The mixture was stirred at room temperature overnight, neutralized with a saturated $NaHCO_3$ aqueous solution, diluted with water, and extracted with $CH_2Cl_2$ (3×20 mL). The combined organic layers were dried over $Na_2SO_4$, concentrated, and purified by chromatography to afford 8,17-epoxide-12-N—(O-methylglycino)-14-deoxyandrographolide (yield: 60%).

MS (m/z): 438.24 (M+1)

$^1$H NMR ($CDCl_3$, 300 MHz): 7.25 (m, 1H), 4.90 (m, 2H), 3.80 (s, 3H), 3.2 (m, 1H), 2.6 (m, 1H), 2.45 (m, 1H), 1.21 (s, 3H), 0.80 (s, 3H).

Example 30

Synthesis 14,15-dehydroandrographolide (Compound 30)

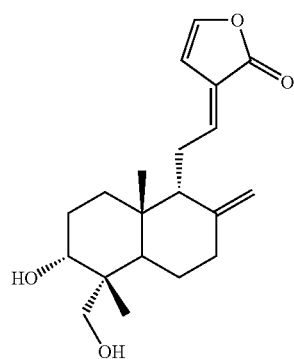

Compound 30

Compound 30 was synthesized according to the method described in Nanduri, et al., *Tetrahedron Letters,* 2004, 45, 4883-4886.

Example 31

Synthesis 11,12-didehydro-19-formyl-14-deoxyandrographolide (Compound 31a) and 11,12-didehydro-19-formyl-3-oxo-14-deoxyandrographolide (Compound 31b)

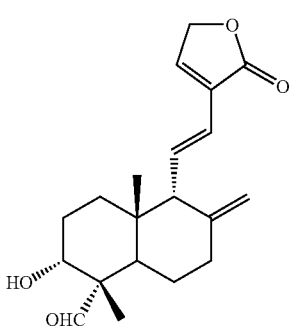

Compound 31a

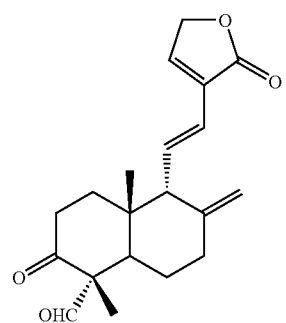

Compound 31b

A solution of 11,12-didehydro-14-deoxyandrographolide (0.86 g, 2 mmol) in 20 mL dichloromethane was added to a mixture of pyridinium chlorochromate (0.87 g, 4 mmol) in 20 mL dichloromethane. The mixture was stirred at room temperature for 5 hours, concentrated, and purified by column chromatography to afford 11,12-didehydro-19-formyl-14-deoxyandrographolide and 11,12-didehydro-19-formyl-3-oxo-14-deoxyandrographolide (yields: 25% and 45%, respectively).

Analytical data for Compound 31a

MS (m/z): 331.18 (M+1)

$^1$H NMR ($CDCl_3$, 300 MHz): 9.81 (s, 1H), 7.20 (m, 1H), 6.8 (m, 1H), 6.1 (m, 1H), 4.91 (s, 1H), 4.88 (m, 2H), 4.52 (s, 1H), 3.25 (m, 1H), 1.3 (s, 3H), 0.7 (s, 3H).

Analytical data for Compound 31b

MS (m/z): 329.18 (M+1)

$^1$H NMR ($CDCl_3$, 300 MHz): 9.82 (s, 1H), 7.25 (m, 1H), 6.7 (m, 1H), 6.1 (m, 1H), 4.94 (s, 1H), 4.88 (m, 2H), 4.55 (s, 1H), 1.25 (s, 3H), 0.8 (s, 3H).

Examples 32-36

Compounds 32-36 were each synthesized in a manner similar to that described in Example 31.

| No. | Name | Structure | NMR |
|---|---|---|---|
| 32 | 12-N-[O-methylglycino]-19-formyl-3-oxo-14-deoxyandrographolide | 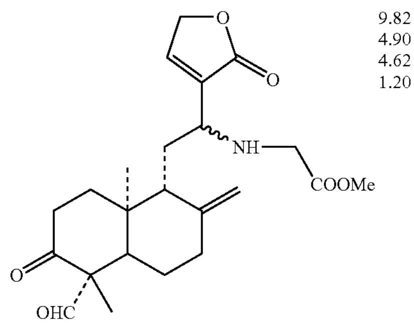 | 9.82 (s, 1H), 7.25 (m, 1H), 4.90 (m, 2H), 4.83 (s, 1H), 4.62 (s, 1H), 3.80 (s, 3H), 1.20 (s, 3H), 0.90 (s, 3H) |
| 33 | 19-formyl-3-oxo-andrographolide | 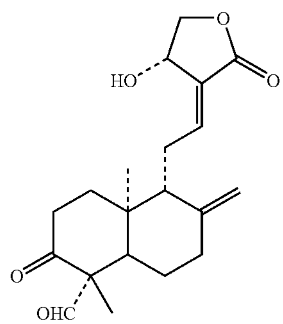 | 9.62 (s, 1H), 7.30 (m, 1H), 4.90 (m, 2H), 4.83 (s, 1H), 4.62 (s, 1H), 4.5 (m, 1H), 1.20 (s, 3H), 0.90 (s, 3H) |
| 34 | 19-formyl-andrographolide | 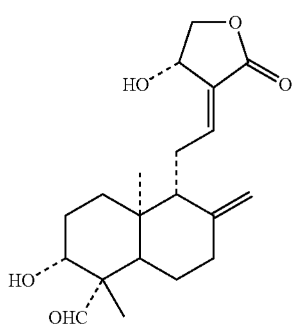 | 9.72 (s, 1H), 7.30 (m, 1H), 4.90 (m, 2H), 4.83 (s, 1H), 4.62 (s, 1H), 4.5 (s, 1H), 3.3 (m, 1H), 1.20 (s, 3H), 0.70 (s, 3H) |
| 35 | 14,15-dehydro-19-formyl-3-oxo-andrographolide | 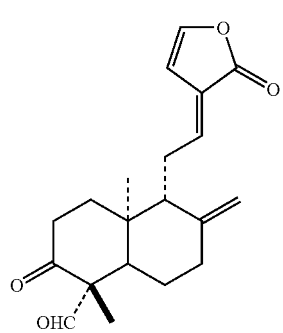 | 9.81 (s, 1H), 7.0 (m, 1H), 6.7 (m, 1H), 6.2 (m, 1H), 1.3 (s, 3H), 0.8 (s, 3H) |

-continued

| No. | Name | Structure | NMR |
|---|---|---|---|
| 36 | 11,12-dihydro-19-formyl-3-oxo-14-deoxyandrographolide | 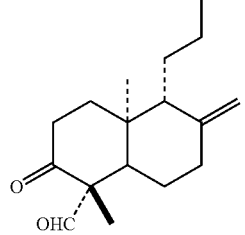 | 9.84 (s, 1H), 7.3 (m, 1H), 2.0 (m, 2H), 1.3 (s, 3H), 0.8 (s, 3H) |

Example 37

Synthesis of 11,12-didehydro-3,19-indazol-14-deoxyandrographolide (Compound 37)

Compound 37

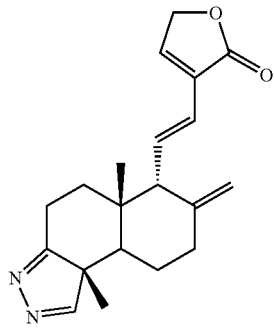

To a solution of 11,12-didehydro-19-formyl-3-oxo-14-deoxyandrographolide (329 mg, 1 mmol) in 20 mL EtOH was added 120 μL $NH_2NH_2.H_2O$ (1.5 mmol). The mixture was stirred at room temperature for 3 hours, diluted with water, and extracted with $CH_2Cl_2$ (3×30 mL). The combined organic layers were washed with brine, dried over $Na_2SO_4$, concentrated, and purified by chromatography to afford the title product (yield: 76%).

MS (m/z): 325.22 (M+1)

$^1$H NMR (CDCl$_3$, 300 MHz): 8.05 (s, 1H), 7.23 (m, 1H), 6.72 (m, 1H), 6.2 (m, 1H), 4.8 (m, 3H), 4.5 (s, 1H), 1.25 (s, 3H), 0.4 (s, 3H).

Examples 38-40

Compounds 38-40 were each synthesized in a manner similar to that described in Example 37.

| No. | Name | Structure | NMR |
|---|---|---|---|
| 38 | 3,19-indazol-andrographolide | 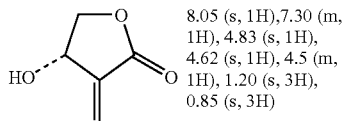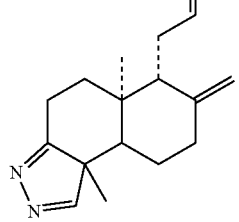 | 8.05 (s, 1H), 7.30 (m, 1H), 4.83 (s, 1H), 4.62 (s, 1H), 4.5 (m, 1H), 1.20 (s, 3H), 0.85 (s, 3H) |

| No. | Name | Structure | NMR |
|---|---|---|---|
| 39 | 3,19-indazol-14,15-dehydro-andrographolide | 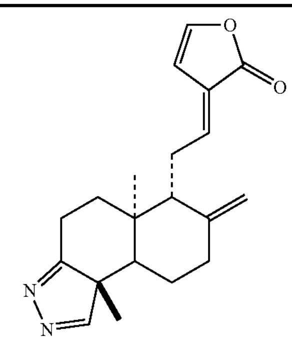 | 8.1 (s, 1H), 7.0 (m, 1H), 6.7 (m, 1H), 6.2 (m, 1H), 4.8 (s, 1H), 4.6 (s, 1H), 1.22 (s, 3H), 0.4 (s, 3H) |
| 40 | 11,12-dihydro-3,19-indazol-14-deoxyandrographolide | 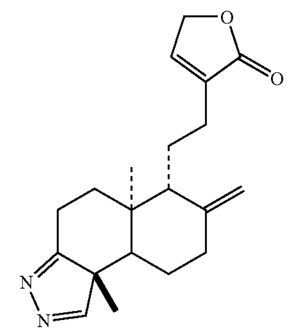 | 8.04 (s, 1H), 7.3 (m, 1H), 4.8 (s, 1H), 4.6 (s, 1H), 2.0 (m, 2H), 1.3 (s, 3H), 0.45 (s, 3H) |

Example 41

Synthesis of 19-dehydroxymethyl-3-oxo-14-acetylandrographolide (Compound 41)

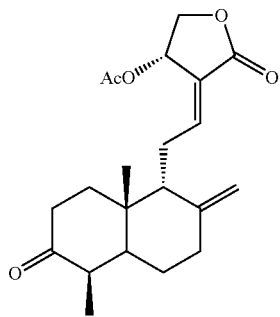

Compound 41

To a solution of 3,19-O-isopropylidiene-14-acetylandrographolide (1.2 g) in THF (30 mL) was added 1N HCl (24 mL). The mixture was stirred at room temperature for 2 hours, and then extracted with ethyl acetate, dried over anhydrous Na$_2$SO$_4$, and concentrated to afford 14-acetylandrographolide (1.0 g).

The above-obtained compound (1.0 g) was dissolved in 25 mL acetone. To this solution was added 3 mL Jone's reagent. The mixture was stirred at 10° C. for 2 hours, diluted with water, and extracted with ethyl acetate (3×30 mL). The combined organic layers were concentrated and purified by silica gel chromatography to afford 19-formyl-3-oxo-14-acetylandrographolide (0.7 g).

A solution of NaClO$_2$ (0.25 g, 2.2 mmol), NaH$_2$PO$_4$ (175 mg, 1.45 mmol) in water (3 mL) was added dropwise at room temperature to a mixture of 19-formyl-3-oxo-14-acetylandrographolide (0.7 g), t-BuOH (10 mL), and 2,3-dimethyl-2-butene (3 mL). The mixture was stirred at room temperature overnight, treated with 1N HCl to adjust the pH to 3, and then extracted with ethyl acetate (4×30 mL). The combined organic layers were washed with brine, dried over MgSO$_4$, concentrated, and purified by column chromatography to afford 19-carboxyl-3-oxo-14-acetylandrographolide (0.5 g).

The above-obtained compound was dissolved in 25 mL ethyl acetate. The solution was heated to reflux for 2 hours, concentrated, and purified by chromatography to afford 0.45 g 19-dehydromethyl-3-oxo-14-acetylandrographolide (yield: 45%).

MS (m/z): 361.19 (M+1)

$^1$H NMR (CDCl$_3$, 300 MHz): 7.03 (m, 1H), 5.9 (m, 1H), 4.85 (s, 1H), 4.80 (m, 2H), 4.61 (s, 1H), 1.1 (s, 3H), 0.95 (d, J=6.3 Hz, 3H).

Examples 42

Synthesis of 12-N-glycinamide-19-dehydroxymethyl-3-oxo-14-deoxyandrographolide (Compound 42)

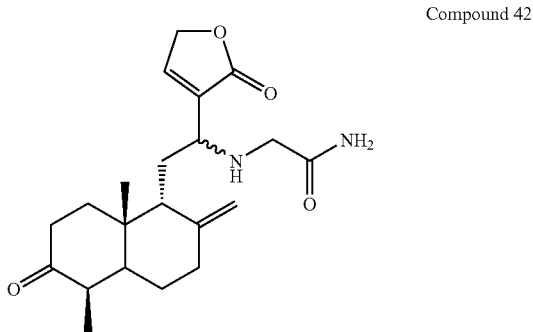

Compound 42

A mixture of glucinamide hydrochloride (0.9 g, 6 mmol) and $K_2CO_3$ (0.82 g, 6 mmol) in 40 mL ethanol was stirred for 15 min. To the mixture was added a solution of 19-dehydroxymethyl-14-acetylandrographolide (0.72 g, 2 mmol) in 50 mL diethyl ether. The organic layer was removed and the aqueous layer was extracted with ethyl acetate (3×50 mL). The combined organic layers were washed with brine, dried over $Na_2SO_4$, concentrated, and purified by chromatography to afford 19-dehydromethyl-12-N-glycinamide-3-oxo-14-deoxyandrographolide (yield: 73%).

MS (m/z): 375.22 (M+1)

$^1$H NMR (CDCl$_3$, 300 MHz): 7.30 (m, 1H), 4.9 (s, 1H), 4.80 (m, 2H), 4.76 (s, 1H), 3.40 (m, 2H), 0.99 (d, J=6.6 Hz, 3H), 0.90 (s, 3H).

Examples 43-47

Compounds 43-47 were each synthesized in a manner similar to that described in Example 42.

| No. | Name | Structure | NMR |
|---|---|---|---|
| 43 | 12-N-benzylamino-19-dehydroxymethyl-3-oxo-14-deoxyandrographolide | 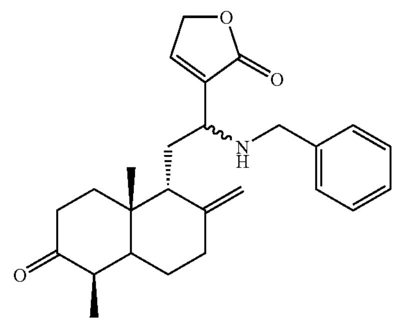 | 7.30 (m, 5H), 7.28 (m, 1H), 4.81 (s, 1H), 4.79 (m, 2H), 4.58 (s, 1H), 1.01 (d, J = 6.6 Hz 3H), 0.88 (s, 3H) |
| 44 | 12-[O-methylglycino]-19-dehydroxymethyl-3-oxo-14-deoxyandrographolide | 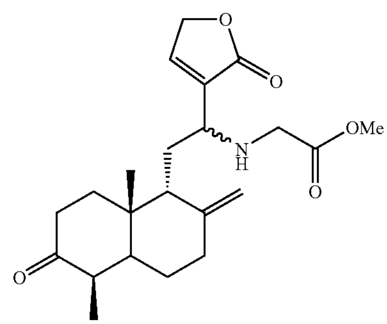 | 7.30 (m, 1H), 4.81 (s, 1H), 4.79 (m, 2H), 4.58 (s, 1H), 3.67 (s, 3H), 1.01 (d, J = 6.6 Hz 3H), 0.88 (s, 3H) |
| 45 | 12-N-[2,2,2-trifluoroethylamino]-19-dehydroxymethyl-3-oxo-14-deoxyandrographolide | 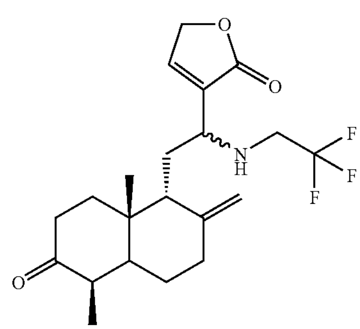 | 7.29 (m, 1H), 4.82 (s, 1H), 4.77 (m, 2H), 4.58 (s, 1H), 3.2 (m, 2H), 1.01 (d, J = 6.6 Hz 3H), 0.88 (s, 3H) |
| 46 | 12-N-[1-pyridin-3-ylmethylamino]-19-dehydroxymethyl-3-oxo-14-deoxyandrographolide | 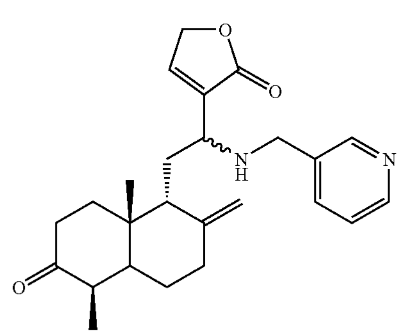 | 8.52 (m, 1H), 8.45 (m, 1H), 7.72 (m, 1H), 7.24 (m, 2H), 4.90 (s, 1H), 4.85 (m, 2H), 4.65 (s, 1H), 0.98 (d, J = 6.6 Hz 3H), 0.90 (s, 3H) |

| No. | Name | Structure | NMR |
|---|---|---|---|
| 47 | 12-N-[methylsulfonylethylamino]-19-dehydroxymethyl-3-oxo-14-deoxyandrographolide | 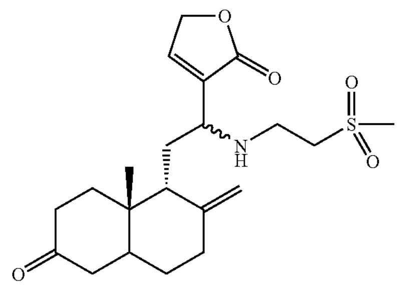 | 7.3 (m, 1H), 5.0 (s, 1H), 4.9 (s, 2H), 4.7 (s, 1H), 3.1 (s, 3H), 0.98 (d, J = 6.4 Hz, 3H), 0.9 (s, 3H) |

Example 48

Synthesis of 12-N-glycinamide-19-dehydroxymethyl-14-deoxyandrographolide (Compound 47)

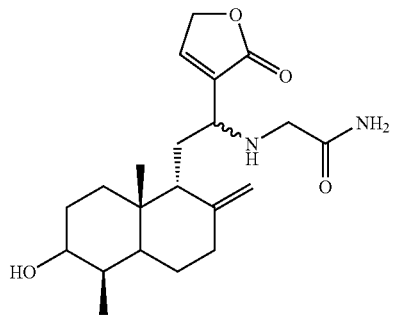

Compound 48

A solution of 12-N-glycinamide-19-dehydromethyl-3-oxo-14-deoxyandrographolide (375 mg, 1 mmol) in 20 mL CH$_3$OH was cooled in an ice-bath. After NaBH$_4$ (45 mg, 1.1 mmol) was added, the mixture was stirred for 2 hours, diluted with water, and extracted with ethyl acetate (3×30 mL). The combined organic layers were washed with brine, dried over Na$_2$SO$_4$, concentrated, and purified by column chromatography to afford the title compound (yield: 85%).

MS (m/z): 377.22 (M+1)

$^1$H NMR (CDCl$_3$, 300 MHz): 7.30 (m, 1H), 4.9 (s, 1H), 4.80 (m, 2H), 4.76 (s, 1H), 3.40 (m, 2H), 3.2 (m, 1H), 0.99 (d, J=6.6 Hz, 3H), 0.92 (s, 3H).

Examples 49-53

Compounds 49-53 were each synthesized in a manner similar to that described in Example 48.

| No. | Name | Structure | NMR |
|---|---|---|---|
| 49 | 12-N-benzylamino-19-dehydroxymethyl-14-deoxyandrographolide | 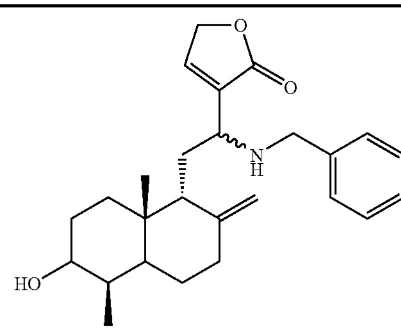 | 7.30 (m, 5H), 7.28 (m, 1H), 4.81 (s, 1H), 4.79 (m, 2H), 4.58 (s, 1H), 3.12 (m, 1H), 0.99 (d, J = 6.6 Hz 3H), 0.88 (s, 3H) |
| 50 | 12-[O-methylglycino]-19-dehydroxymethyl-14-deoxyandrographolide | 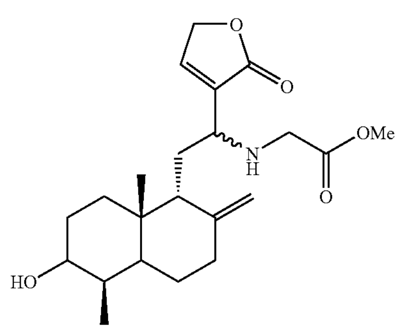 | 7.30 (m, 1H), 4.81 (s, 1H), 4.79 (m, 2H), 4.58 (s, 1H), 3.75 (s, 3H), 3.2 (m, 1H), 1.00 (d, J = 6.6 Hz 3H), 0.88 (s, 3H) |

| No. | Name | Structure | NMR |
|---|---|---|---|
| 51 | 12-N-[2,2,2-trifluoroethylamino]-19-dehydroxymethyl-14-deoxyandrographolide | 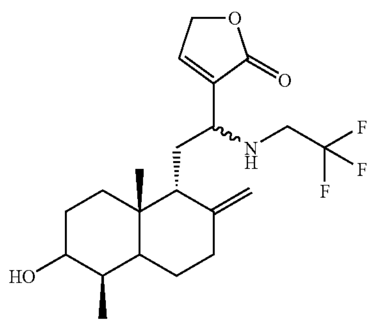 | 7.29 (m, 1H), 4.82 (s, 1H), 4.77 (m, 2H), 4.58 (s, 1H), 3.2 (m, 2H), 3.15 (m, 1H), 1.01 (d, J = 6.6 Hz 3H), 0.88 (s, 3H) |
| 52 | 12-N-[1-pyridin-3-ylmethylamino]-19-dehydroxymethyl-14-deoxyandrographolide | 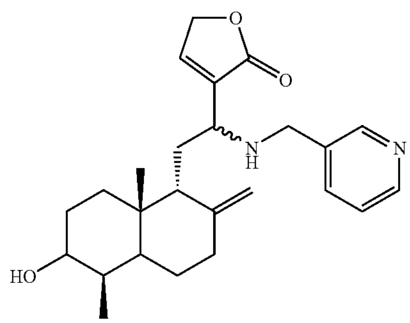 | 8.52 (m, 1H), 8.45 (m, 1H), 7.72 (m, 1H), 7.24 (m, 2H), 4.90 (s, 1H), 4.85 (m, 2H), 4.65 (s, 1H), 3.20 (m, 1H), 0.98 (d, J = 6.6 Hz 3H), 0.90 (s, 3H) |
| 53 | 19-dehydroxymethyl-andrographolide | 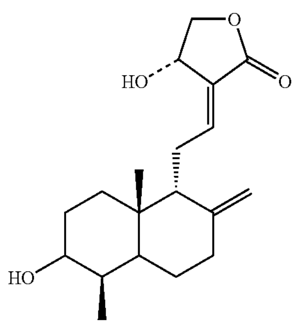 | 7.30 (m, 1H), 4.90 (m, 2H), 4.83 (s, 1H), 4.62 (s, 1H), 4.5 (s, 1H), 3.3 (m, 1H), 1.0 (d, J = 6.6 Hz, 3H), 0.90 (s, 3H) |

Example 54

Synthesis of 12-N-glycinamide-19-dehydroxymethyl-3-hydroxyimino-14-deoxyandrographolide (Compound 54)

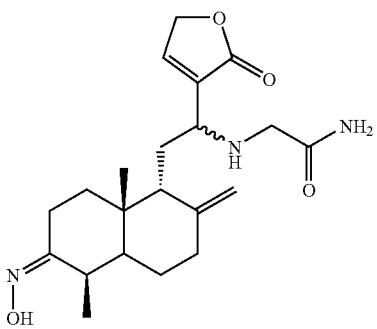

Compound 54

To a solution of 12-N-glycinamide-19-dehydroxymethyl-3-oxo-14-deoxyandrographolide (750 mg, 2 mmol) in 20 mL dioxane was added $NH_2OH \cdot HCl$ (188 mg, 2.6 mmol) and pyridine (215 μL, 2.6 mmol). The mixture was stirred at 40° C. for 3 hours, concentrated, and then purified by chromatography to afford the title product (yield: 55%).

MS (m/z): 389.23 (M+1)

$^1$H NMR (CDCl$_3$, 300 MHz): 7.25 (m, 1H), 4.92 (s, 1H), 4.80 (m, 2H), 4.76 (s, 1H), 3.40 (m, 2H), 1.01 (d, J=6.6 Hz, 3H), 0.88 (s, 3H).

Example 55

Synthesis of 19-N-methylamino-andrographolide (Compound 55)

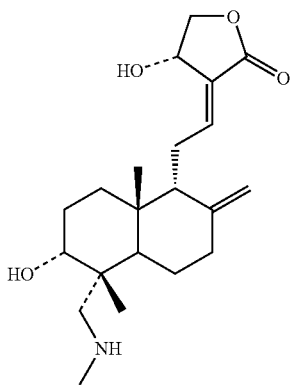

Compound 55

A mixture of 19-formyl-andrographolide (540 mg, 1.6 mmol), $CH_3NH_2 \cdot HCl$ (125 mg, 1.6 mmol) and $NaBHCN_3$ (240 mg, 3.2 mmol) in 20 mL $CH_2Cl_2$ and 5 mL $C_2H_5OH$ was heated to reflux for 30 minutes and then stirred at room temperature for 2 hours. The mixture was diluted with water and extracted with $CH_2Cl_2$ (3×20 mL). The combined $CH_2Cl_2$ layers were washed with brine, dried over $Na_2SO_4$, concentrated, and purified by chromatography to afford the title product (yield: 62%).

MS (m/z): 363.24 (M+1)

$^1$H NMR (CDCl$_3$, 300 MHz): 7.30 (m, 1H), 4.90 (m, 2H), 4.83 (s, 1H), 4.62 (s, 1H), 4.5 (s, 1H), 3.3 (m, 1H), 2.5 (s, 3H), 1.20 (s, 3H), 0.70 (s, 3H).

Example 56

Inhibition of TNFα-Induced NF-κB Activation

Human Embryonic Kidney (HEK) 293 cells were purchased from American Tissue Culture Collection (ATCC; Manassas, Va.) and cultured in DMEM containing 10% FBS at 37° C. under 5% $CO_2$. The cells were cotransfected with pNFκB-luc and pcDNA3.1. Stably transfected pNFκB-luc-293 clones were selected in the presence of G418 (0.6 mg/mL) and seeded in a 96-well plate at 3×10$^4$ cells/well.

For each of the above-synthesized compounds, a series of DMEM solutions at different concentrations were prepared and added to wells containing selected HEK 293 cells. The final compound concentrations in the wells were 0.1, 0.3, 1, 3, or 10 µM. After being incubated for 15 minutes, the cells were stimulated by 10 ng/mL recombinant human TNFα for 4 hours. Wells containing 0.1 µg/mL triptolide and 10 ng/mL recombinant human TNFα were used as the positive control. Wells containing 10 µl DMEM media and 10 ng/mL recombinant human TNFα were used as the negative control. Wells containing 10 µl DMEM media, not TNFα and the tested compounds were used as the background.

The treated cells were lysed, and luciferase activity was measured by the Luciferase Assay System (Promega, Wis., USA) using a Perkin-Elmer Victor 3 plate reader. The NF-κB activation inhibition ratio of each compound was calculated as:

[1−(compound treatment−background)/(negative control−background)]×100%

The results show that all of the tested compounds inhibited TNFα-induced NF-κB activation.

Example 57

Inhibition of TNFα, IL-1β, and iNOS expression

THP-1 cells (human monocytic cells) and RAW 264.7 cells (Mouse leukemic monocyte macrophage cells) were purchased from American Tissue Culture Collection (ATCC; Manassas, Va.). The cells were cultured in RPMI 1640 or DMEM containing 10% FBS at 5×10$^3$ cells/well.

For each of the above-synthesized compounds, a series of DMEM solutions at different concentrations were prepared and added to wells containing THP-1 cells or RAW 264.7 cells. The final compound concentrations in the wells were 0.1, 0.3, 1, 3, or 10 µM. Wells containing 10 µM dexamethasone (an anti-inflammatory drug) were used as the positive control. Wells containing 10 µl DMEM media were used as the background. The plate was incubated at 37° C. under 5% $CO_2$ for 15 minutes. For cytokines induction, 10 µl of 10 µg/ml LPS was added to each well except the background well and the cells were placed in a 37° C., 5% $CO_2$ incubator for 1 hour. For iNOS mRNA induction, 10 µl of 10 µg/ml LPS and 200 ng/mL mIFN-γ were added to each well except the background well and the cells were placed in a 37° C., 5% $CO_2$ incubator for 8 hours. Finally, THP-1 cells were treated with a lysis buffer containing TNFα or IL-1β target probes at 53° C. for 0.5 hour. RAW264.7 cells were treated with a lysis buffer containing iNOS target probes at 53° C. for 0.5 hour.

The lysate of the cells were analyzed using bDNA assay kits (QuantiGene™, GenoSpectra, US) according to the manufacturer's protocol. Oligonucleotide probes derived from human TNFα (GenBank NM_000594), human IL-1β (GenBank NM_000576), and mouse inducible nitric oxide synthase 2 (iNOS, GenBank NM_010927) were synthesized by Invitrogen Biotechnology Company (Shanghai, China). Cell lysate was transferred to wells of a capture plate (100 µl/well) and incubated at 53° C. for 16 to 20 hours. After the capture plate was washed with washing buffer, 100 µl Amplifier Working Reagent was added to each well and the plate was incubated at 53° C. for 1 hour. After the plate was washed, 100 µl Label Working Reagent was added to each well, followed by being incubated at 53° C. for 1 hour. Then, after the plate was washed again, 100 µl Substrate Working Reagent was added to each well. After incubation for 0.5 hour at 46° C., luminescence of each well was measured using a Perkin-Elmer Victor III plate reader. The inhibition ratio for each compound was calculated as:

[1−(compound treatment−background)/(stimuli treatment−background)]×100%

The results show that the tested compounds all inhibited the mRNA expression of TNFα, IL-1β, and/or iNOS. Their $IC_{50}$ ranged from 0.1 to 10 µM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention can be made and used to practice this invention. Thus, other embodiments are also within the claims.

What is claimed is:
1. A compound of formula (I):

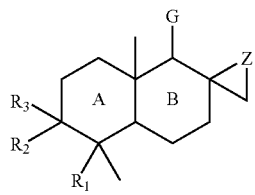

formula (I)

in which
R₁ is H, OH, CHO, or CH₂NR$_a$R$_b$, each of R₂ and R₃, independently, is H, OH, or NR$_a$R$_b$ or R₂ and R₃ together are =O or =NR$_c$; or R₁ is CH₂OH, each of R₂ and R₃, independently, is H, or NR$_a$R$_b$, or R₂ and R₃ together are =O or =NR$_c$;
in which each of R$_a$ and R$_b$ independently, is H, alkyl, cycloalkyl, aryl, or heteroaryl chosen from pyridinyl, imidazolyl, thienyl and thiazolyl, and R$_c$ is H, alkyl, cycloalkyl, aryl, heteroaryl chosen from pyridinyl, imidazolyl, thienyl and thiazolyl, hydroxy, or alkoxy;
or R₁, R₂, and R₃, together with ring A which they are attached to, are:

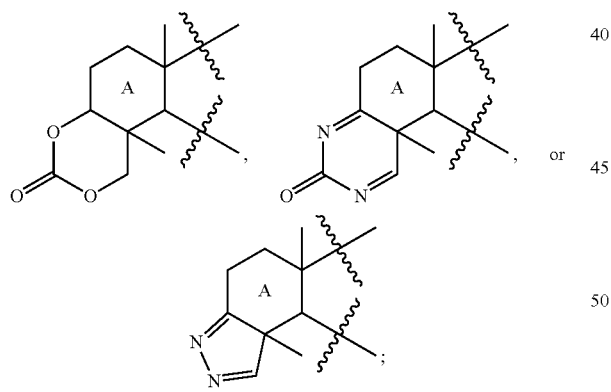

G is:

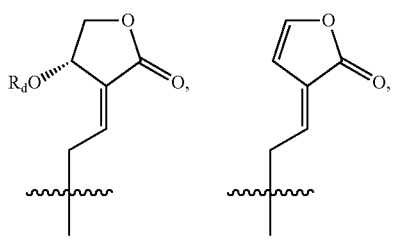

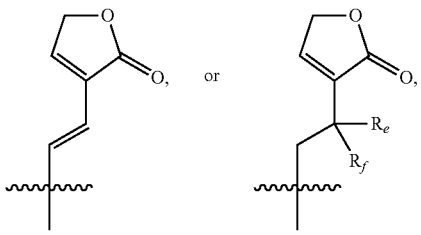

in which R$_d$ is H, alkyl, cycloalkyl, aryl, heteroaryl chosen from pyridinyl, imidazolyl, thienyl and thiazolyl, R$_a$CO, or R$_a$R$_b$NHCO, each of R$_a$′ and R$_b$′, independently, being H, alkyl, cycloalkyl, aryl, or heteroaryl chosen from pyridinyl, imidazolyl, thienyl and thiazolyl; each of R$_e$ and R$_f$ independently, is H, alkoxy, aryloxy, heteroaryloxy wherein the heteroaryl is chosen from pyridinyl, imidazolyl, thienyl and thiazolyl, alkylthio, arylthio, heteroarylthio wherein the heteroaryl is chosen from pyridinyl, imidazolyl, thienyl and thiazolyl, or NR$_c$′R$_d$′, R$_c$′ and R$_d$′, independently, being H, alkyl, cycloalkyl, aryl, or heteroaryl chosen from pyridinyl, imidazolyl, thienyl and thiazolyl; and Z is O or a bond,
and/or at least one pharmaceutically acceptable salt thereof.

2. The compound of claim 1, wherein the formula (I) is

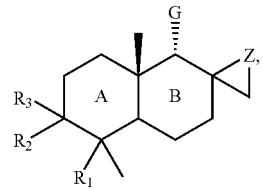

in which R₁, R₂, R₃, G, and Z are defined in claim 1.

3. The compound of claim 2, wherein R₁, R₂, and R₃, together with ring A which they are attached to, are:

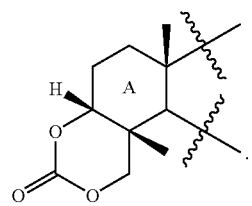

4. The compound of claim 2, wherein R₁ is H, and R₂ and R₃ together are =O; or each of R₁ and R₂ is H, and R₃ is OH.

5. The compound of claim 2, wherein G is

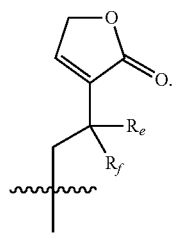

in which $R_e$ and $R_f$ are as defined in claim 1.

6. The compound of claim 5, wherein $R_1$, $R_2$, and $R_3$, together with ring A which they are attached to, are:

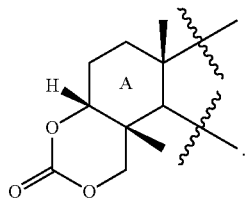

7. The compound of claim 6, wherein Z is a bond.

8. The compound of claim 7, wherein $R_e$ is H and $R_f$ is heteroaryl chosen from pyridinyl, imidazolyl, thienyl and thiazolyl; or $R_e$ is H and $R_f$ is $NR_cR_{d'}$, $R_{c'}$ being H and $R_{d'}$ being alkyl.

9. The compound of claim 5, wherein $R_1$ is H, and $R_2$ and $R_3$ together are =O.

10. The compound of claim 9, wherein Z is a bond.

11. The compound of claim 10, wherein $R_e$ is H and $R_f$ is heteroaryl chosen from pyridinyl, imidazolyl, thienyl and thiazolyl; or $R_e$ is H and $R_f$ is $NR_cR_{d'}$, $R_{c'}$ being H and $R_{d'}$ being alkyl.

12. The compound of claim 5, wherein each of $R_1$ and $R_2$ is H, and $R_3$ is OH.

13. The compound of claim 12, wherein Z is a bond.

14. The compound of claim 13, wherein $R_e$ is H and $R_f$ is heteroaryl chosen from pyridinyl, imidazolyl, thienyl and thiazolyl; or $R_e$ is H and $R_f$ is $NR_cR_{d'}$, $R_{c'}$ being H and $R_{d'}$ being alkyl.

15. The compound of claim 2, wherein G is

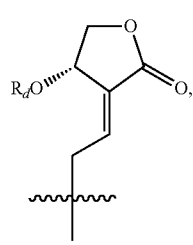

in which $R_d$ is defined in claim 1.

16. The compound of claim 15, wherein $R_1$, $R_2$, and $R_3$, together with ring A which they are attached to, are:

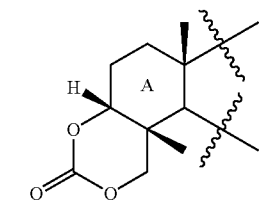

17. The compound of claim 15, wherein $R_1$ is H, and $R_2$ and $R_3$ together are =O; or each of $R_1$ and $R_2$ is H, and $R_3$ is OH.

18. The compound of claim 2, wherein Z is a bond.

19. The compound of claim 18, wherein $R_1$, $R_2$, and $R_3$, together with ring A which they are attached to, are:

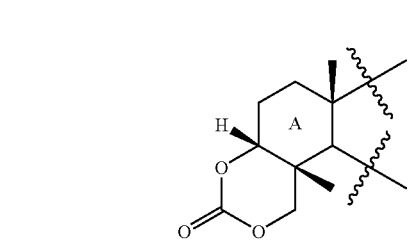

20. The compound of claim 18 wherein $R_1$ is H, and $R_2$ and $R_3$ together are =O; or each of $R_1$ and $R_2$ is H, and $R_3$ is OH.

21. The compound of claim 2, wherein $R_1$ is CHO, $R_2$ is OH, and $R_3$ is H.

22. At least one compound chosen from:

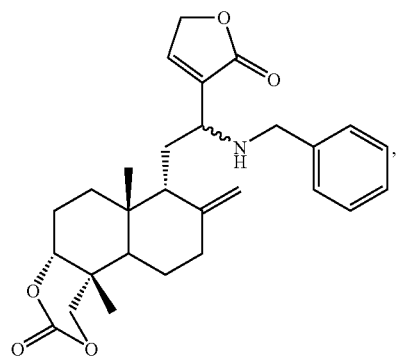

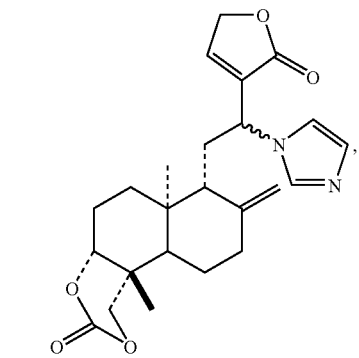

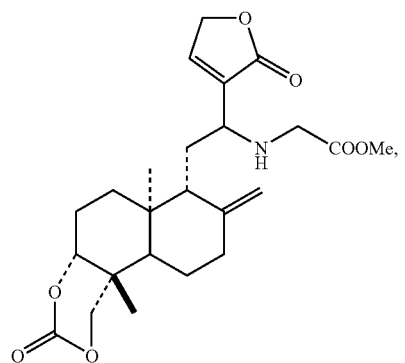
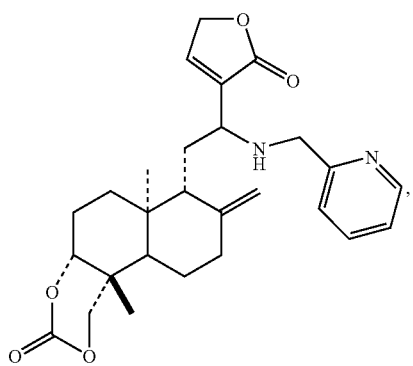
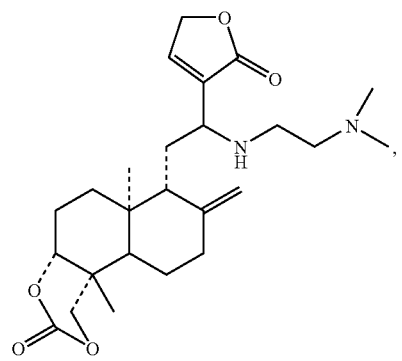
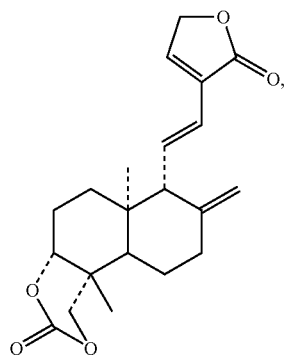
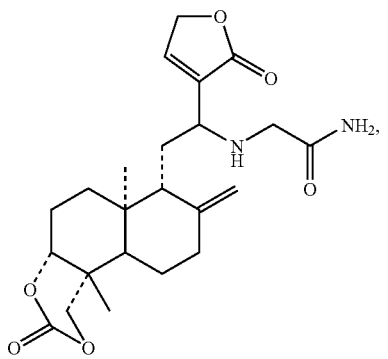
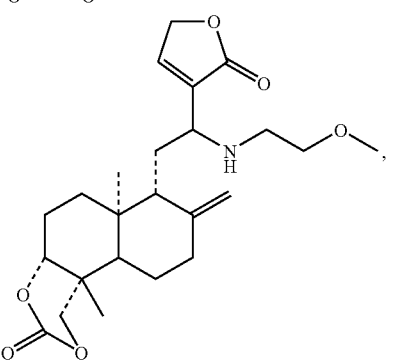
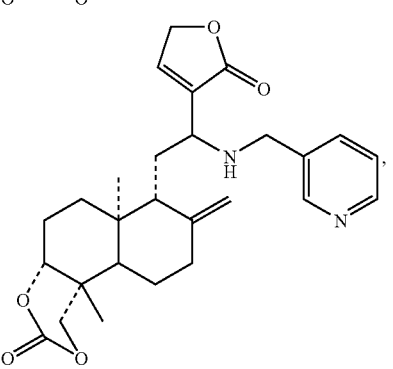
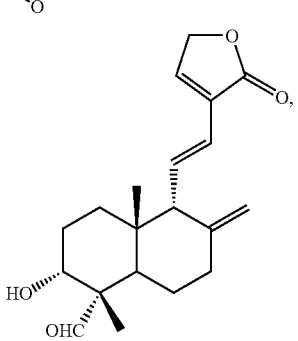
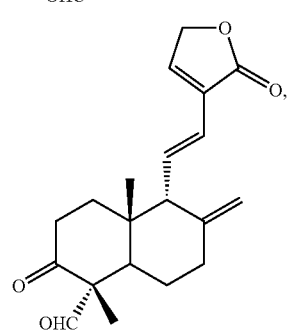

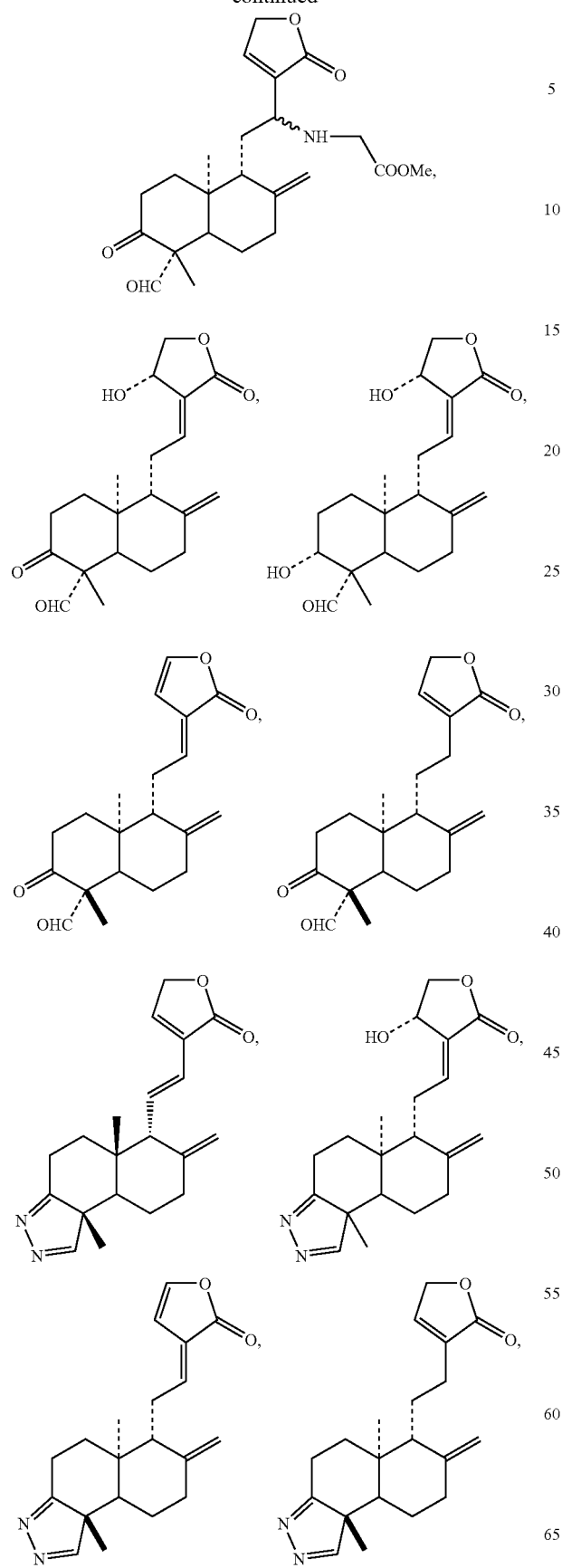
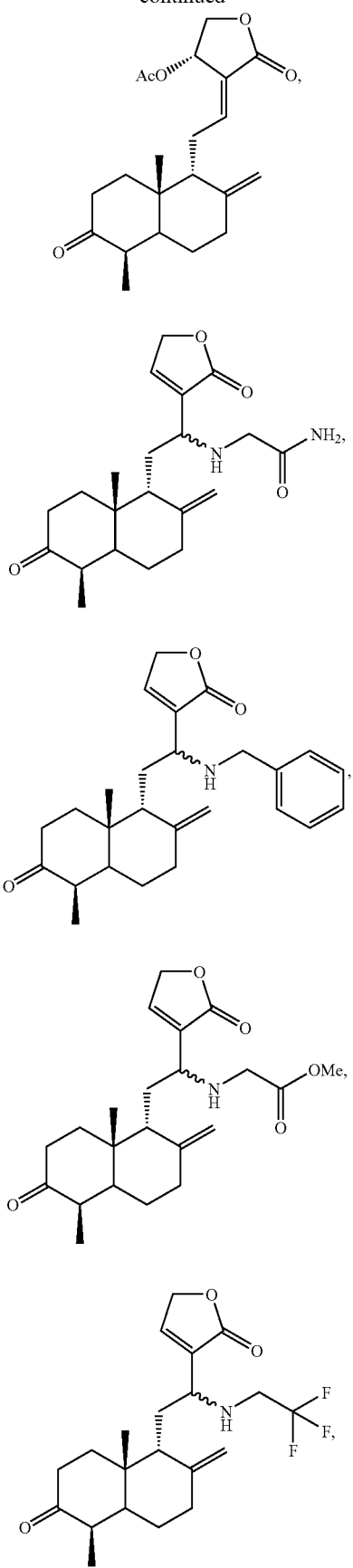

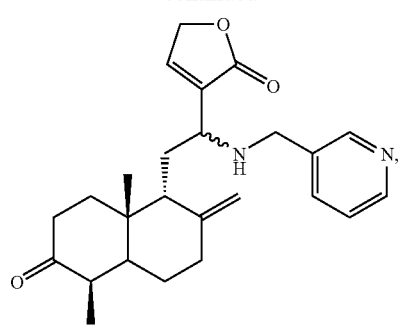
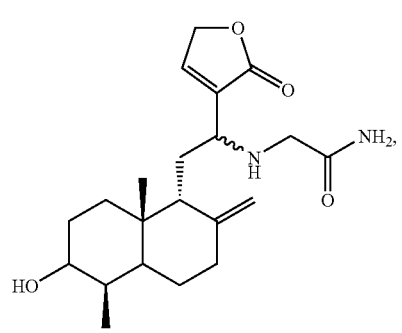
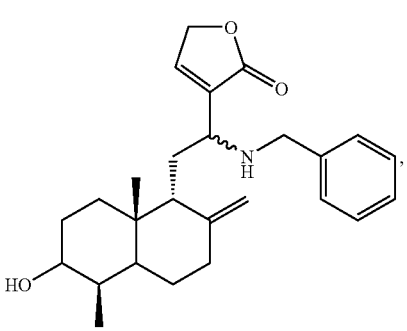
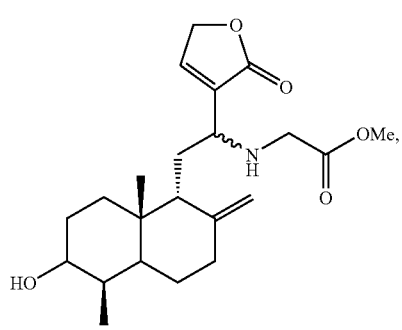
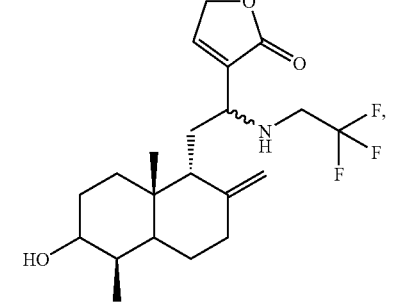
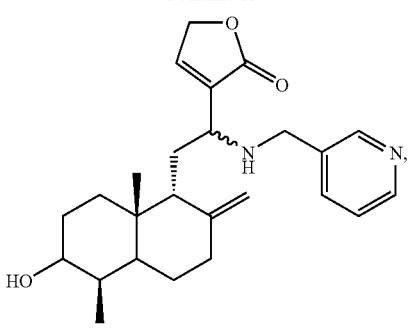
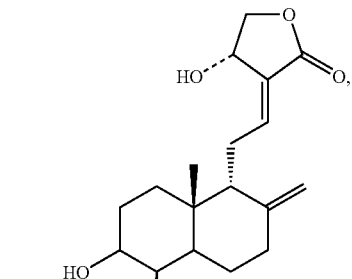
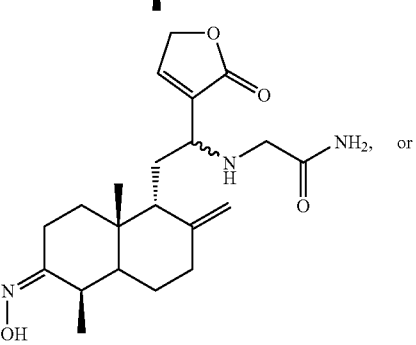
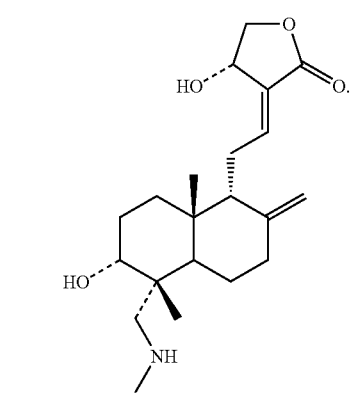
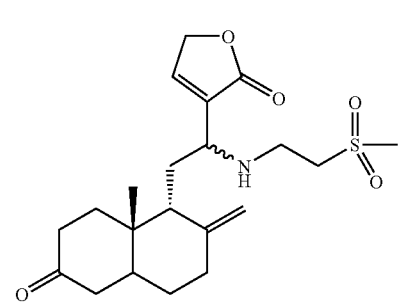

and/or at least one pharmaceutically acceptable salt thereof.

23. A method of inhibiting TNFα-induced NF-κB activation in a cell in need thereof, comprising contacting the cell with an effective amount of at least one compound of claim 1.

24. A method of inhibiting TNFα, IL-1β, or iNOS expression in a cell in need thereof, comprising contacting the cell with an effective amount of at least one compound of claim 1.

* * * * *

UNITED STATES PATENT AND TRADEMARK OFFICE
CERTIFICATE OF CORRECTION

PATENT NO.         : 7,902,359 B2                                       Page 1 of 4
APPLICATION NO.    : 11/954010
DATED              : March 8, 2011
INVENTOR(S)        : Wang et al.

It is certified that error appears in the above-identified patent and that said Letters Patent is hereby corrected as shown below:

On the Title Page, Item (74), in the "*Attorney, Agent, or Firm*", line 2,
"Farrabow, Garrett & Dunner LLP" should read
--Farabow, Garrett & Dunner, LLP--.

On the Title Page, Item (57), in the Abstract, line 5, "to is methods"
should read --to methods--.

In claim 5, column 49, lines 4-12,

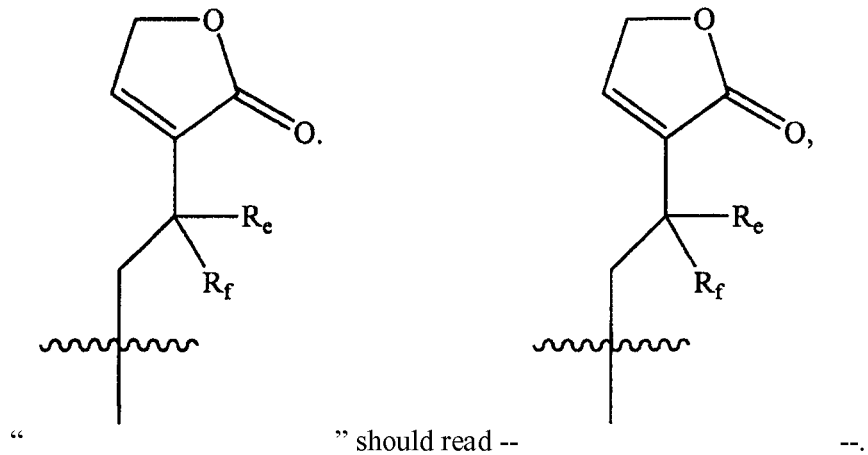

" " should read -- --.

Signed and Sealed this
Fourteenth Day of June, 2011

David J. Kappos
*Director of the United States Patent and Trademark Office*

CERTIFICATE OF CORRECTION (continued)
U.S. Pat. No. 7,902,359 B2

In claim 22, column 56, lines 27-38,

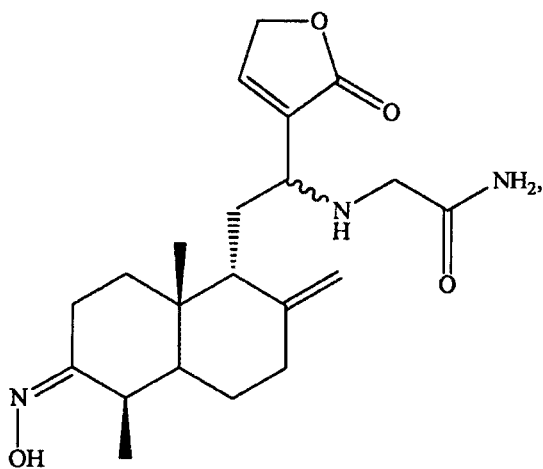

after " 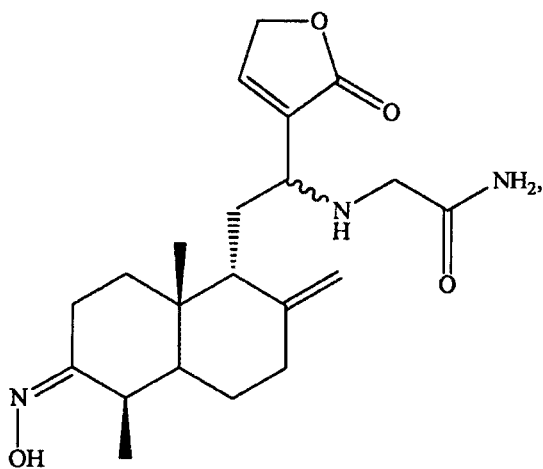 ", delete "or".

CERTIFICATE OF CORRECTION (continued)
U.S. Pat. No. 7,902,359 B2

Page 3 of 4

In claim 22, column 56, lines 40-54,

" 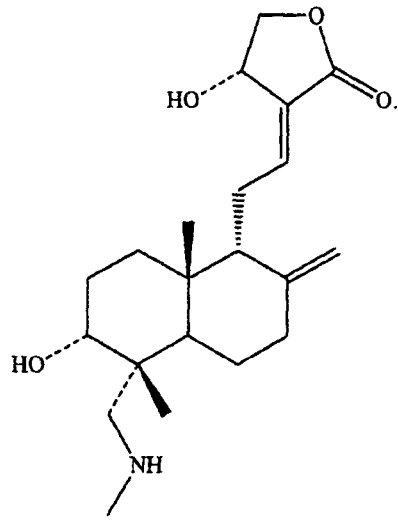 " should read

-- 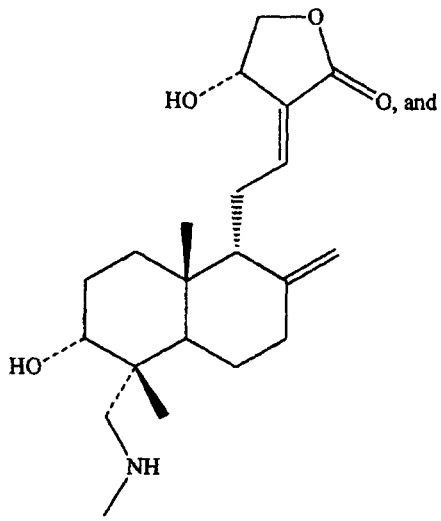 --.

CERTIFICATE OF CORRECTION (continued)
U.S. Pat. No. 7,902,359 B2

In claim 22, column 56, lines 56-67,

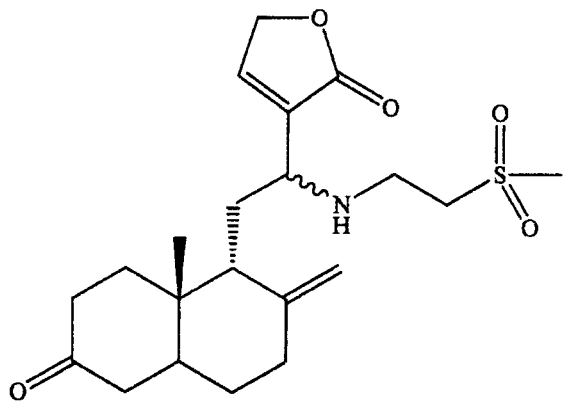

after " 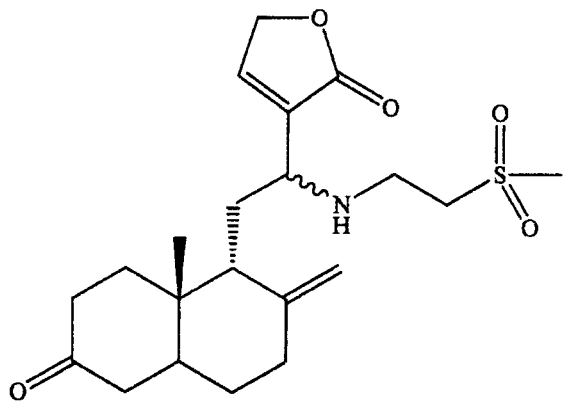 ", insert --,--.